US012582781B2

(12) United States Patent  
Chitnis et al.

(10) Patent No.: US 12,582,781 B2  
(45) Date of Patent: Mar. 24, 2026

(54) INJECTION SYSTEMS AND METHODS OF THEIR USE

(71) Applicant: MeiraGTx Ocular UK Limited, London (GB)

(72) Inventors: Girish Chitnis, Belmont, MA (US); Jeff Karp, Chestnut Hill, MA (US); Edward Ahn, Dover, MA (US); Bryan Laulicht, New York, NY (US)

(73) Assignee: MeiraGTx Ocular UK Limited, London (GB)

( * ) Notice: Subject to any disclaimer, the term of this patent is extended or adjusted under 35 U.S.C. 154(b) by 875 days.

(21) Appl. No.: 17/761,481

(22) PCT Filed: Sep. 20, 2020

(86) PCT No.: PCT/US2020/051702  
§ 371 (c)(1),  
(2) Date: Mar. 17, 2022

(87) PCT Pub. No.: WO2021/055906  
PCT Pub. Date: Mar. 25, 2021

(65) Prior Publication Data  
US 2022/0379044 A1 Dec. 1, 2022

Related U.S. Application Data

(60) Provisional application No. 63/052,518, filed on Jul. 16, 2020, provisional application No. 62/903,406, filed on Sep. 20, 2019.

(51) Int. Cl.  
A61M 5/46 (2006.01)  
A61F 9/00 (2006.01)  
(Continued)

(52) U.S. Cl.  
CPC ............ A61M 5/46 (2013.01); A61F 9/0008 (2013.01); A61J 1/2096 (2013.01);  
(Continued)

(58) Field of Classification Search  
CPC .... A61M 5/31596; A61M 5/28; A61M 5/283; A61M 5/31513; A61M 5/3129;  
(Continued)

(56) References Cited

U.S. PATENT DOCUMENTS

| | | | | |
|---|---|---|---|---|
| 3,253,592 A | * | 5/1966 | Von Pechmann | ..... A61M 5/178 |
| | | | | D24/114 |
| 3,368,558 A | * | 2/1968 | Sarnoff | ................... A61M 5/24 |
| | | | | 604/203 |

(Continued)

FOREIGN PATENT DOCUMENTS

| | | |
|---|---|---|
| CN | 102026599 A | 4/2011 |
| CN | 101588842 B | 9/2013 |

(Continued)

OTHER PUBLICATIONS

International Search Report and Written Opinion in PCT International Application No. PCT/US2020/051702 mailed Dec. 17, 2020.

(Continued)

*Primary Examiner* — Laura A Bouchelle  
(74) *Attorney, Agent, or Firm* — Fox Rothschild LLP

(57) ABSTRACT

An injection system comprising a syringe barrel; a first sealing element and a second sealing element moveably disposed in the syringe barrel; an injection chamber between them; a puncture element extending from the first sealing element to deliver an injection agent from the injection chamber into a biological space, wherein one or more of the syringe barrel, the first or the second sealing element are configured to prevent proximal movement of the first sealing element past a pre-selected location, while allowing the (Continued)

second sealing element to come in contact with the first sealing element, the system is configured such that, when a force is applied on the second sealing element in a distal direction, in response to a first opposing force, the puncture element advances and in response to a second opposing force, the puncture element remains stationary and the injection agent is conveyed through the puncture element.

26 Claims, 18 Drawing Sheets

(51) Int. Cl.
| | |
|---|---|
| *A61J 1/20* | (2006.01) |
| *A61M 5/315* | (2006.01) |
| *A61M 5/32* | (2006.01) |

(52) U.S. Cl.
CPC ...... *A61M 5/31505* (2013.01); *A61M 5/3221* (2013.01); *A61M 2210/0612* (2013.01)

(58) Field of Classification Search
CPC .... A61M 2005/1787; A61M 2005/287; A61M 2005/3131; A61F 9/0008; A61J 1/2096
See application file for complete search history.

(56) References Cited

U.S. PATENT DOCUMENTS

| | | | |
|---|---|---|---|
| 3,923,058 | A | 12/1975 | Weingarten |
| 4,064,879 | A | 12/1977 | Leibinsohn |
| 4,067,333 | A | 1/1978 | Reinhardt et al. |
| 4,275,730 | A | 6/1981 | Hussein |
| 4,394,863 | A | 7/1983 | Bartner |
| 4,624,659 | A | 11/1986 | Goldberg et al. |
| 4,869,717 | A | 9/1989 | Adair |
| 4,932,941 | A | 6/1990 | Min et al. |
| 5,106,372 | A | 4/1992 | Ranford |
| 5,120,314 | A * | 6/1992 | Greenwood ........ A61M 5/5013 604/110 |
| 5,215,523 | A | 6/1993 | Williams et al. |
| 5,270,685 | A | 12/1993 | Hagen et al. |
| 5,722,955 | A | 3/1998 | Racz |
| 5,902,273 | A | 5/1999 | Yang et al. |
| 6,050,974 | A | 4/2000 | Allard et al. |
| 6,200,289 | B1 | 3/2001 | Hochman et al. |
| 6,719,736 | B2 | 4/2004 | Collins et al. |
| 7,025,774 | B2 | 4/2006 | Freeman et al. |
| 7,351,223 | B2 | 4/2008 | Call |
| 7,918,814 | B2 | 4/2011 | Prausnitz et al. |
| 7,967,777 | B2 | 6/2011 | Edwards et al. |
| 8,034,105 | B2 | 10/2011 | Stegmann et al. |
| 8,123,729 | B2 | 2/2012 | Yamamoto et al. |
| 8,172,830 | B2 | 5/2012 | Christian et al. |
| 8,197,435 | B2 | 6/2012 | Prausnitz et al. |
| 8,287,491 | B2 | 10/2012 | Burns et al. |
| 8,291,768 | B2 | 10/2012 | Spiegel et al. |
| 8,419,764 | B2 | 4/2013 | Begg |
| 8,636,713 | B2 | 1/2014 | Prausnitz et al. |
| 8,808,225 | B2 | 8/2014 | Prausnitz et al. |
| 8,920,388 | B2 | 12/2014 | Slocum et al. |
| 9,180,047 | B2 | 11/2015 | Andino et al. |
| D750,223 | S | 2/2016 | Andino et al. |
| 9,539,139 | B2 | 1/2017 | Andino et al. |
| 9,572,800 | B2 | 2/2017 | Zarnitsyn et al. |
| 9,636,253 | B1 | 5/2017 | Andino et al. |
| 9,636,332 | B2 | 5/2017 | Zarnitsyn et al. |
| 9,770,361 | B2 | 9/2017 | Andino et al. |
| 9,788,995 | B2 | 10/2017 | Prausnitz et al. |
| 9,931,330 | B2 | 4/2018 | Zarnitsyn et al. |
| 9,937,075 | B2 | 4/2018 | Andino et al. |
| 9,956,114 | B2 | 5/2018 | Andino et al. |
| 10,188,550 | B2 | 1/2019 | Andino et al. |
| 10,390,901 | B2 | 8/2019 | Godfrey et al. |
| 10,517,756 | B2 | 12/2019 | Andino et al. |
| 10,555,833 | B2 | 2/2020 | Andino et al. |
| 11,129,932 | B2 * | 9/2021 | Meenken ................ A61M 5/28 |
| 11,413,397 | B2 | 8/2022 | Karp et al. |
| 2002/0035351 | A1 | 3/2002 | Iodice |
| 2003/0199846 | A1 | 10/2003 | Fowles et al. |
| 2004/0171984 | A1 | 9/2004 | Greenfield |
| 2005/0182370 | A1 | 8/2005 | Hato |
| 2005/0277880 | A1 | 12/2005 | Shue et al. |
| 2007/0100288 | A1 | 5/2007 | Bozeman et al. |
| 2008/0208137 | A1 * | 8/2008 | Fago ................. A61M 5/31596 604/236 |
| 2009/0018506 | A1 | 1/2009 | Daily et al. |
| 2009/0318864 | A1 | 12/2009 | Carrel et al. |
| 2011/0224642 | A1 | 9/2011 | Fojtik |
| 2012/0041379 | A1 * | 2/2012 | Macarthur ............ A61M 5/282 604/93.01 |
| 2012/0095409 | A1 | 4/2012 | Anin et al. |
| 2012/0271272 | A1 | 10/2012 | Hammack et al. |
| 2013/0216623 | A1 | 8/2013 | Yamamoto et al. |
| 2015/0045769 | A1 | 2/2015 | Aquino et al. |
| 2015/0051581 | A1 | 2/2015 | Andino et al. |
| 2015/0182700 | A1 | 7/2015 | Bang |
| 2015/0258120 | A1 | 9/2015 | Zarnitsyn et al. |
| 2017/0354791 | A1 | 12/2017 | Lewkonya et al. |
| 2018/0028357 | A1 | 2/2018 | Prausnitz et al. |
| 2018/0028516 | A1 | 2/2018 | Zarnitsyn et al. |
| 2018/0092897 | A1 | 4/2018 | Zarnitsyn et al. |
| 2018/0325884 | A1 | 11/2018 | Zarnitsyn et al. |
| 2019/0117901 | A1 | 4/2019 | Szapiro et al. |
| 2019/0240208 | A1 | 8/2019 | Zarnitsyn et al. |
| 2020/0030143 | A1 | 1/2020 | Andino et al. |
| 2023/0046514 | A1 | 2/2023 | Karp et al. |

FOREIGN PATENT DOCUMENTS

| | | | |
|---|---|---|---|
| CN | 105246529 | B | 6/2019 |
| DE | 202004011516 | U1 | 1/2006 |
| EP | 1360968 | A1 | 11/2003 |
| EP | 2380622 | A1 | 10/2011 |
| JP | 4505561 | B1 | 10/1992 |
| JP | 2005-349179 | A | 12/2005 |
| JP | 2016-520383 | A | 7/2016 |
| WO | WO 2009023247 | A1 | 2/2009 |
| WO | WO 2009089409 | A1 | 7/2009 |
| WO | WO 2013022604 | A1 | 2/2013 |
| WO | 2013173129 | A2 | 11/2013 |
| WO | WO 2013191394 | A1 | 12/2013 |
| WO | WO 2014028285 | A1 | 2/2014 |
| WO | WO 2014074823 | A1 | 5/2014 |
| WO | WO 2016060925 | A1 | 4/2016 |
| WO | 2018112305 | A1 | 6/2018 |
| WO | WO 2021055906 | A1 | 3/2021 |

OTHER PUBLICATIONS

Chitnis et al., "A Resistance-Sensing Mechanical Injector for the Precise Delivery of Liquids to Target Tissue", Nat. Biomed. Eng., vol. 3 pp. 621-631, Aug. 3, 2019.
Extended European Search Report in European Application No. 20866654.5 mailed Oct. 9, 2023.
Search Report dated Sep. 12, 2024 in corresponding ARIPO Application No. AP/P/2022/013995.
Reasons for Rejection dated Aug. 19, 2024 in corresponding Japanese Application No. 2022-518353.
Notice of Reason for Rejection issued Jan. 15, 2025 in corresponding Japanese Patent Application No. 2022-518353, 14 pgs.

* cited by examiner

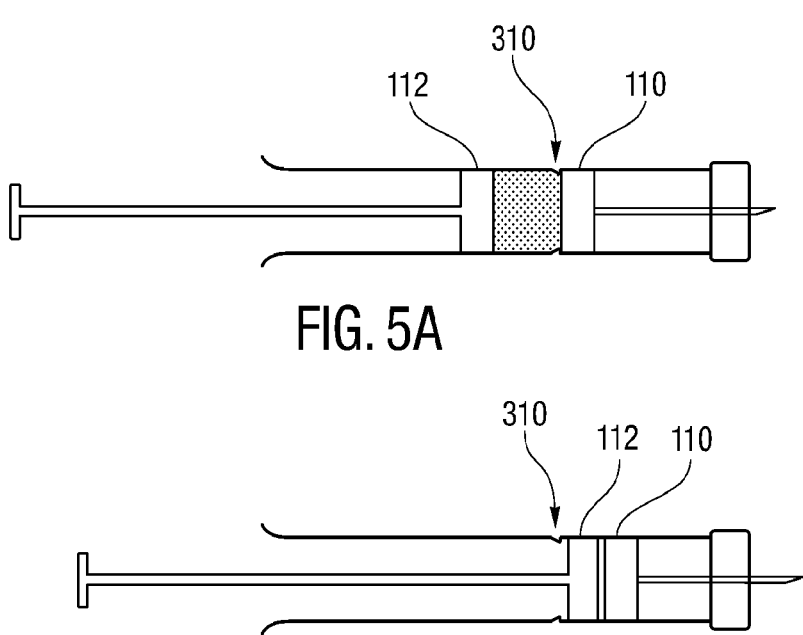
FIG. 5A
FIG. 5B
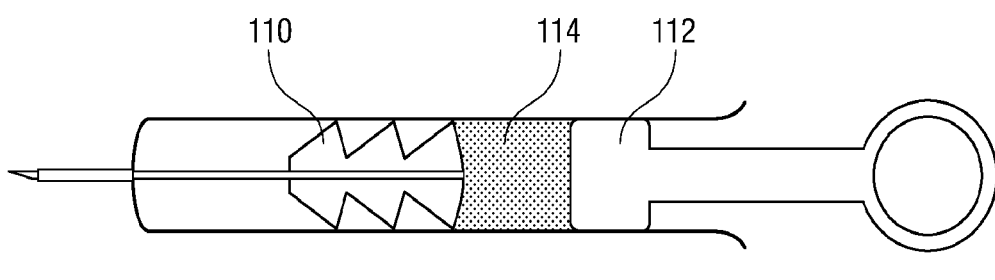
FIG. 6A
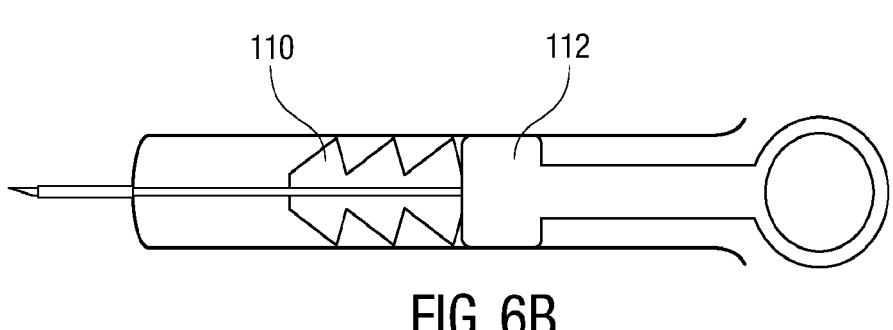
FIG. 6B

Strategic cuts
(NON peripheral)

Form to achieve
the bend

Insert in barrel and
affix to the walls

INJECTION SYSTEMS AND METHODS OF THEIR USE

CROSS-REFERENCE TO RELATED APPLICATION

This application is a national phase filing under 35 U.S.C. 371 of International Application No. PCT/US2020/051702, filed Sep. 20, 2020, which claims the benefit of and priority to U.S. Provisional Application No. 63/052,518 filed Jul. 16, 2020 and U.S. Provisional Application No. 62/903,406 filed Sep. 20, 2019, and the contents of these applications are hereby incorporated herein by reference in their entireties.

FIELD

The present disclosure is related to a system and method that enables an injection into a cavity or a void, and in particular through a tissue into a cavity or void in a human body, such as the suprachoroidal space in ocular tissue.

BACKGROUND

Posterior segment eye diseases are a major cause of permanent visual impairment affecting millions of people which can lead to blindness if left untreated. It includes multiple diseases such as age-related macular degeneration (AMD), diabetic retinopathy, diabetic macular edema (DME), choroidermeia (CHM), retinal vein occlusion (RVO), uveitis, and endophthalmitis. Although pharmaceutical agents may be available to prevent disease progression in many cases, systemic delivery cannot achieve therapeutic concentrations in the posterior segment due to the blood-eye barrier.

Local delivery through topical, transscleral and intravitreal routes can be effective but higher concentrations are needed at the site of delivery to maintain therapeutic concentration at the diseased site of retina after diffusion through vitreous. There are also reports about intraocular implants for continuous delivery, but they can be significantly more invasive than intravitreal injections. To increase the concentration at the diseased site of the retina, subretinal injections have also been performed. Subretinal injections, however, require a demanding, inconsistent technique that must be performed in a surgical setting, result in sparse, spotty coverage and create the risk of retinal detachment. Furthermore, repeat dosing with subretinal injections may not be possible or desirable because additional injection can further damage the diseased and frail retina. There have been additional strategies reported to accelerate the movement of drug molecules to retina such as iontophoresis and magnetic field which adds another level of complication to the overall drug delivery problem.

Recently, the suprachoroidal space (SCS) has been explored as the potential drug delivery route to the back of the eye. The suprachoroidal space is the potential space between the sclera and the choroid. Drug delivered in this space can go around the eye globe to the posterior segment of the eye. This route for drug delivery has been shown to be more effective for treatment of posterior segment than intravitreal injections. However, the simplicity of intravitreal injection outweighs the surgical procedure previously needed for suprachoroidal delivery. Historically, suprachoroidal delivery was achieved by creating small incision using scalpel, followed by delivery using a puncture element or cannula. More recently, a micropuncture element with a predefined, short length, which allows penetration only up to certain depth, has been used to target suprachoroidal space. Because the scleral thickness varies significantly within the patient populations, either prior mapping of eye geometry, or trial and error, is necessary while injecting with hollow micropuncture elements. If the puncture element is too long, it can easily penetrate through the thin suprachoroidal space to inject the drug in the vitreous; and, if it is too short, it delivers into the sclera. The sclera is 10 times stiffer than the choroid and 200 stiffer than the retina making it even more challenging to pierce the sclera without injecting into the vitreous. In some instances, a small volume (on the order of 100 microliters) of therapeutic needs to be injected into the suprachoroidal space, and it needs to be injected with sufficient force to displace the positive resistance of intraocular pressure pressing the choroid against the sclera to achieve a broad coverage of the posterior segment of the eye.

Accordingly, there is a need for an improved system and method for suprachoroidal drug delivery that precisely, consistently and safely targets the suprachoroidal space and provides broad coverage of the posterior segment of the eye.

SUMMARY

In some aspects, the present disclosure provides an injection system comprising: a syringe barrel defining a lumen between a proximal end and a distal end; a first sealing element moveably disposed within the lumen, a second sealing element moveably disposed within the lumen proximal to the first sealing element, wherein the first sealing element and the second sealing element form a seal with the lumen and define an injection chamber between them; a puncture element extending from a distal end of the first sealing element, the puncture element being in fluid communication with the injection chamber to deliver an injection agent from the injection chamber into a space in a tissue of a patient, wherein one or more of the syringe barrel, the first sealing element, and the second sealing element are configured to prevent proximal movement of the first sealing element past a pre-selected location, while allowing the second sealing element to come in contact with the first sealing element, and wherein the system is configured such that, when a force is applied on the second sealing element in a distal direction, in response to a first opposing force, the first sealing element moves in the distal direction to advance the puncture element in the distal direction, without conveying the injection agent through the puncture element, and in response to a second opposing force, the first sealing element remains stationary and the injection agent is conveyed from the injection chamber through the puncture element. In some embodiments, the first opposing force is due to backpressure exerted on the puncture element as the puncture element advances through the tissue; and the second opposing force is due to backpressure exerted on the puncture element as the puncture element opens into the space in the tissue, in sonic embodiments, the force applied on the second sealing element is sufficient to advance the first sealing element but is insufficient to convey the injection agent through the puncture element in response to the first opposing force; and the force applied on the second sealing element is insufficient to advance the first sealing element but is sufficient to convey the injection agent through the puncture element in response to the second opposing force.

In some embodiments, a unidirectional stop is disposed in the syringe barrel between the first sealing element and the second sealing element, the unidirectional stop being configured to prevent a proximal movement of the first sealing element past the unidirectional stop, while allowing the second sealing element to pass through the mechanical stop to contact the first sealing element. The unidirectional stop can comprise a section of the syringe barrel having a reduced diameter, wherein the first sealing element has a diameter sufficiently larger than the reduced diameter such that the first sealing element cannot pass through the section while the second sealing element is configured to pass through the section to contact the first sealing element. In sonic embodiments, the unidirectional stop comprises a portion of an inner surface of the syringe barrel having a friction coefficient sufficient to prevent a proximal movement of the first sealing element. In some embodiments, the unidirectional stop comprises a mechanical stop. In some embodiments, the unidirectional stop comprises a foldable stop disposed between the first sealing element and the second sealing element, the foldable stop being configured to prevent a proximal movement of the first sealing element past the foldable stop and being configured to fold upon application of a force in a distal direction on the foldable stop to allow the second sealing element to pass through the foldable stop to contact the first sealing element. In some embodiments, the first sealing element is shaped such that a frictional or sliding force on the first sealing element in the proximal direction is higher than a frictional or sliding force on the first sealing element in the distal direction and is higher than a force of insertion of the puncture element into the tissue.

In some embodiments, in a relaxed state, the first sealing element has a size that is between 1.01 to 2 times larger than a size of the lumen of the syringe barrel. In some embodiments, in a relaxed state, the first sealing element has a size that is between 1.01 to 1.10 times larger than a size of the lumen of the syringe barrel. In some embodiments, in a relaxed state, the first sealing element has a size that is between 1.01 to 1.4 times larger than a size of the lumen of the syringe barrel. An inner surface of the syringe barrel can be modified to increase friction between the inner surface of the syringe barrel and the first sealing element. In some embodiments, a lock is disposed distally of the first sealing element and configured to selectively lock the first sealing element in place. The lock can include a sealed compartment defined in the lumen of the syringe barrel distal to the first sealing element, an incompressible substance inside the compartment, and a valve to release the incompressible substance from the compartment, such that when the valve is closed, a distal movement of the first sealing element is prevented and, when the valve is open, the distal movement of the first sealing element is allowed.

In some embodiments, a touch trigger mechanism is disposed between the first sealing element and the second sealing element, the touch trigger mechanism is configured to deploy when the first sealing element comes in contact with the second sealing element to prevent a distal movement of the first sealing element. In some embodiments, a fill port is disposed on a surface of the syringe barrel and being in fluid communication with the injection chamber, in some embodiments, such fill port can comprise a receptacle disposed on an outside surface of the syringe barrel and configured to receive a vial: a flowpath connecting the receptacle and the injection chamber; a self-sealing member configured to seal the flowpath and a puncture element disposed in the receptacle, the puncture element being configured to pierce through the self-sealing member to fluidly connect a vial received in the receptacle with the injection chamber. In some embodiments, the puncture element is moveable relative to the receptacle such that,

4 when the vial is received in the receptacle, the puncture element is moved toward the injection chamber to pierce the self-sealing member and to fluidly connect the vial with the injection chamber, when the medicament container removed from the receptacle, the puncture element is moved away from the injection chamber, thereby allowing the self-sealing member to seal the flowpath.

In some embodiments, a support element is disposed about a distal portion of the puncture element, the support element being moveable in relation to the puncture element and the syringe barrel. The injection chamber can comprise a first chamber and a second chamber, wherein a chamber sealing portion of the second sealing element fluidly isolates the first chamber from the second chamber, such that a movement of the chamber sealing portion fluidly connects the first and second chambers. In some embodiments, the injection chamber comprises a first chamber and a second chamber, wherein the first chamber and the second chamber are fluidly isolated from one another when the second sealing element is in an initial position and wherein a movement of the second sealing element fluidly connects the first and second chambers. In some embodiments, the second sealing element is configured to engage the first sealing element and to withdraw the first sealing element and the puncture element into the syringe barrel.

In sonic aspects, the present disclosure provides a method for treatment of an eye disease, the method comprises: pre-inserting into a sclera of a patient a puncture element of an injection system, the injection system comprising: a syringe barrel defining a lumen between a proximal end and a distal end; a first sealing element moveably disposed within the lumen; a second sealing element moveably disposed within the lumen proximal to the first sealing element, wherein the first sealing element and the second sealing element form a seal with the lumen and define an injection chamber between them; the puncture element extending from a distal end of the first sealing element, the puncture element being in fluid communication with the injection chamber to deliver an injection agent from the injection chamber into a space in a tissue of a patient; and wherein one or more of the syringe barrel, the first sealing element, and the second sealing element are configured to prevent proximal movement of the first sealing element past a pre-selected location, while allowing the second sealing element to come in contact with the first sealing element; advancing the puncture element through the sclera by applying a force onto the second sealing element, the force being sufficient to move the first sealing element in the distal direction to advance the puncture element in the distal direction, without conveying the injection agent through the puncture element; and maintaining the force onto the second sliding element as the puncture element passes through the sclera and opens into a suprachoroidal space (SCS) such that the injection agent is conveyed from the injection chamber through the puncture element into the SCS, without further distal movement of the first sealing element. In some embodiments, the eye disease is age-related macular degeneration (AMD), diabetic macular edema (DME), glaucoma, retinal vein occlusion (RVO), uveitis, endophthalmitis, Stargardt disease, Leber Congenital Amaurosis (LCA), Retinitis Pigmentosa, or Choroideremia. In some embodiments, the injection fluid comprises one or more injection agent formulations comprising a viral delivery vector comprising a gene of interest and a promoter selected to promote the gene of interest. The gene of interest can be an anti-VEGFR2 gene, the delivery vector can be an AAV vector, a promoter for the anti-VEGFR2 gene can be a CAG promoter. In some embodiments, the injection fluid comprises one or more injection agent formulations comprising an anti-VEGFR2 compound selected from a group consisting of bevacizumab, ranibizumab, aflibercept, Ramucirumab, disintegrins, anti-prostaglandins, tryptophanyl-tRNAsynthetase-derived poly-peptides, Inosine monophosphate dehydrogenase (IMPDH) inhibitors and anti-PDGF to treat AMD; and corticosteroids to treat uveitis, chorioretinitis, or other inflammatory eye diseases; botulinum toxin for various ocular applications; tyrosine kinase inhibitors.

In some aspects, the present disclosure provides a kit for injection of an injection agent into a tissue comprising: an injection system comprising: a syringe barrel defining a lumen between a proximal end and a distal end; a first sealing element moveably disposed within the lumen; a second sealing element moveably disposed within the lumen proximal to the first sealing element, wherein the first sealing element and the second sealing element form a seal with the lumen and define an injection chamber between them; a puncture element extending from a distal end of the first sealing element, the puncture element being in fluid communication with the injection chamber to deliver an injection agent from the injection chamber into a space in a tissue of a patient; and wherein one or more of the syringe barrel, the first sealing element, and the second sealing element are configured to prevent proximal movement of the first sealing element past a pre-selected location, while allowing the second sealing element to come in contact with the first sealing element, and wherein the system is config-ured such that, when a force is applied on the second sealing element in a distal direction, in response to a first opposing force, the first sealing element moves in the distal direction to advance the puncture element in the distal direction, without conveying the injection agent through the puncture element, and in response to a second opposing force, the first sealing element remains stationary and the injection agent is conveyed from the injection chamber through the puncture element; and a volume of the injection fluid comprising one or more injection agent formulations. In some embodiments, the eye disease is age-related macular degeneration (AMD), diabetic macular edema (DME), glaucoma, retinal vein occlusion (RVO), uveitis, endophthalmitis, Stargardt dis-ease, Leber Congenital Amaurosis (LCA), Retinitis Pigmen-tosa, or Choroideremia. In some embodiments, the injection fluid comprises one or more injection agent formulations comprising a viral delivery vector comprising a gene of interest and a promoter selected to promote the gene of interest. The gene of interest can be an anti-VEGFR2 gene, the delivery vector can be an AAV vector, a promoter for the anti-VEGFR2 gene can be CAG promoter. In some embodi-ments, the injection fluid comprises one or more injection agent formulations comprising an anti-VEGFR2 compound selected from a group consisting of bevacizumab, ranibi-zumab, aflibercept, Ramucirumab, disintegrins, anti-prosta-glandins, tryptophanyl-tRNAsynthetase-derived polypep-tides, Inosine monophosphate dehydrogenase (IMPDH) inhibitors and anti-PDGF to treat AMD; and corticosteroids to treat uveitis, chorioretinitis, or other inflammatory eye diseases; botulinum toxin for various ocular applications; tyrosine kinase inhibitors.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 5A-5B show an embodiment of an injection system of the present disclosure with a reduction in a diameter of the syringe barrel.

FIGS. 6A-6B show embodiments of an injection system of the present where a sealing element is shaped to have an asymmetrical frictional force;

Figure 1A:
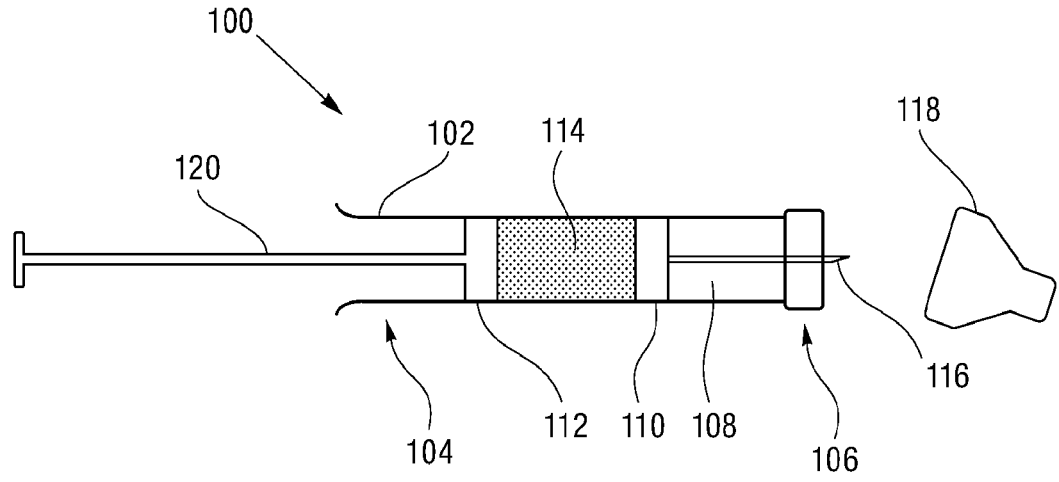
FIG. 1A shows an embodiment of an injection system of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Accordingly, there is a need for an improved system and method for injection of an agent into a biological space, existing or potential (such as, suprachoroidal space) that precisely, consistently and safely targets such space and provides broad coverage of adjacent structures or organs. For example, the injection systems of the present disclosure can be used for drug delivery into the suprachoroidal space to provide broad coverage of the of the posterior segment of the eye. The presently disclosed injection systems are configured that the puncture element automatically stops at the interface of the target space, thus limiting the depth that the needle penetrates into the cavity. The injection system of the present disclosure can thus be configured to self-adjust the depth of penetration of the puncture element into the target space. The presently disclosed injection systems can be used to penetrate a tissue (for example, sclera) and deliver an injection agent into a biological space (such as, suprachoroidal space), while self-regulating the depth of penetration into the biological space and site of the injection based on the resistance the system encounters during different stages of the delivery cycle. In some embodiments, the precision and miniaturization of the injection system of the present disclosure allows the puncture element to precisely target and stop at a thin potential cavity, such as the suprachoroidal space, and allows the accurate delivery of a precise volume of an injection agent with broad coverage. In some embodiment, the volume may be sub-milliliter. In some embodiments, the injection systems of the present disclosure are configured to deliver a therapeutic to a target space with microliter accuracy.

The following description of the injection systems of the present disclosure and methods of their use provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In reference to FIG. 1, an injection system of the present disclosure may include a syringe barrel 102 having a proximal end 104 and a distal end 106 and defining a lumen 108 between the proximal end 104 and the distal end 106. The injection system further includes a first sealing element 110 and a second sealing element 112 both slidably disposed within the lumen 108 of the syringe barrel 102. As shown in FIG. 1, in an initial state, the first sealing element 110 and the second sealing element 112 are spaced apart from one another and the space between the sealing elements in the syringe barrel defines an injection chamber 114 for holding a suitable volume of an injection agent therein. The term "injection agent" as used herein refers to a composition comprising a single substance or a combination of substances that can be injected into a space or potential space in a tissue. The injection agent may be presented as a fluid, liquid, gas, suspension, solution, emulsion or another flowable composition. In some embodiments, the injection agent may include one or more therapeutic substances or formulations, including, but not limited to, a small molecule chemical compound, antibody, nucleic acid molecule, a polypeptide as well as compounds to aid in delivery of the foregoing to the patient, for example, viruses or vectors for delivery of nucleic acids. In some embodiments, a standard syringe barrel can be used having a volume between 10 ul to 50 ml. In some embodiments, the injection chamber can have a volume of between about 0.025 ml and 20 ml, but larger or smaller syringe barrels can also be used. In some embodiments, the injection chamber can have a volume of approximately 0.025 ml, 0.05 ml, 0.1 ml, 0.5 ml, 1 ml, 3 ml, 5 ml, or 10 ml prior to the displacement of the injection agent.

The sealing elements 110 and 112 can fit tightly into the syringe barrel 102 and form a seal with the walls of the syringe barrel 102 to keep the injection agent from leaking from the injection chamber 114. In some embodiments, the second sealing element can be slid or screwed to move relative to the syringe barrel. Thus, in some embodiments, the device disclosed herein does not require feedback (e.g. haptic, tactile) by the operator. In some embodiments, the sealing elements frictionally interact with the walls of the syringe barrel as the sealing elements slide along the lumen of the syringe barrel. In some embodiments, the size and shape of the sealing agents can be varied to change the frictional force between the sealing elements and the syringe barrel. In some embodiments, the sealing elements can be made of a natural or synthetic polymer such as, for example, natural or synthetic rubbers or elastomeric materials.

In some embodiments, a puncture element 116 extends from a distal end of the first sealing element, a lumen of the puncture element being in fluid communication with the injection chamber to deliver the injection agent from the injection chamber into a target injection space. The puncture element may be protected by a safety cap 118 during storage, transportation and handling of the injection system. In operation, as is described in more detail below, a force may be applied to the second sealing element, using a push rod 120, in the distal direction or forward force. This force causes the second sealing element to move forward, pressurize the injection agent and apply a forward force on the first sealing element. Depending on the force in the proximal direction on the puncture element (backpressure or opposing force), the first sealing element moves in the distal direction to advance the puncture element in the distal direction, without conveying the injection agent through the puncture element, or the first sealing element remains stationary and the injection agent is conveyed from the injection chamber through the puncture element. Accordingly, for the ease of understanding, the first sealing element may be referred to as a floating sealing element and the second sealing element may be referred to as a pushing sealing element.

The term "puncture element" refers to a device that can be used to penetrate a tissue and to deliver injection agent to a space or potential space in the tissue. In some embodiments, the puncture element can be a generally elongated device with a sharpened end that can be used to puncture and penetrate a tissue. The puncture member can have any number of suitable dimensions and/or geometries. For example, the puncture element may have a circular or non-circular cross-section. In some embodiments, the puncture element may have one or more lumens for delivering the injection agent to a target space or potential space in the tissue, with each of the one or more lumens having one or more openings at the end of the lumen or along the sides.

Figure 1B:
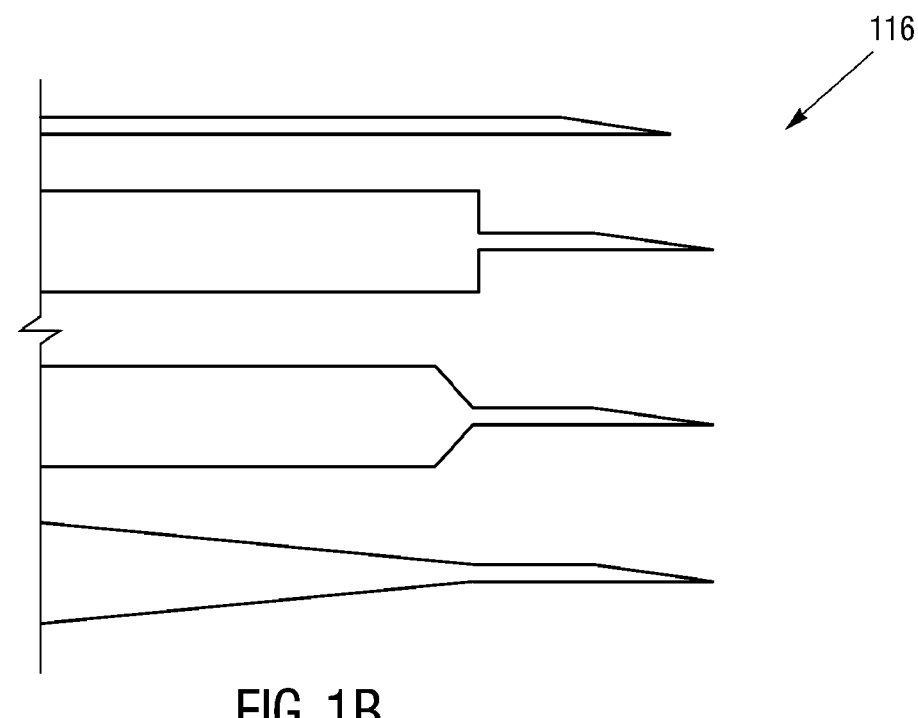
FIG. 1B illustrates various embodiments of a puncture element suitable for use in connection with an injection system of the present disclosure.

FIG. 1B illustrates various embodiments of puncture elements that can be used in connection with the injection system of the present disclosure. In some embodiments, the puncture element has variable diameter to improve delivery of viscous agents while keeping the part of the puncture element being inserted into the eye of small diameter (e.g. 30 G, 27 G.). In some embodiments, the puncture element tip bevel geometry is designed to minimize the insertion force and bevel by modifying cutting edge inclination, number of bevels, and rake angles and the insertion force. The puncture element tip geometries include, but are not limited to, bevel tip, lancet point, back bevel tip and curved tip. The puncture element with lower insertion force typically is easier for guidance and has less deflection.

In some embodiments, the puncture element comprises a standard needle between 34 G and 25 G. In some embodiments, the puncture element may be a standard 30 G needle. In some embodiments, the puncture element can be 25 gauge and higher, 27 gauge and higher, or 30 gauge or higher. In some embodiments the needle has a secondary bevel to lower cutting forces. However, various puncture element sizes and shapes can be used in connection with the injection system of the present disclosure. In some embodiments, particularly for higher viscosity formulations, puncture elements with larger lumens may be used. It should be noted that various other sizes, shapes and geometries can be used depending on the desired result and operating parameters, for example, viscosity of the injection agent, density of tissue into which the puncture element is inserted, desired flow rate of the injection agent and similar parameters.

The puncture element can be connected to the floating sealing element using multiple techniques. In some embodiments, the puncture element is inserted into the floating sealing element and secured with waterproof adhesive. In some embodiments, the floating sealing element could be molded around the puncture element. In some embodiments, a puncture element with threads on the outer surface could be screwed into the floating sealing element.

Figures 2, 3:
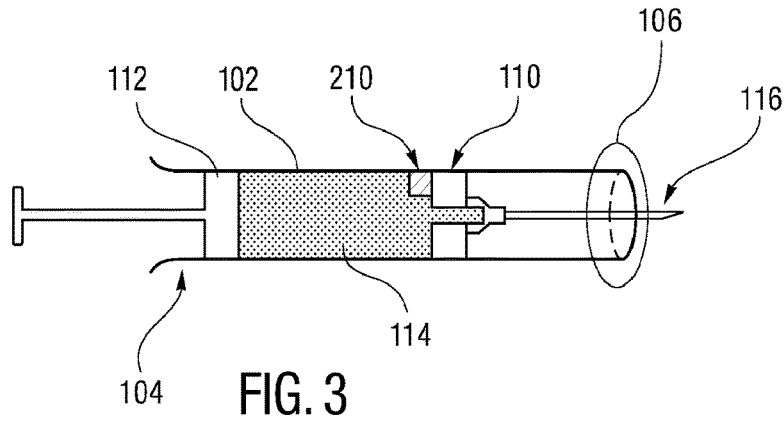
FIG. 2 illustrates an exemplary method of use of an embodiment of an injection system of the present disclosure.
FIG. 3 shows an embodiment of an injection system of the present disclosure having a one-way stop.

In reference to FIG. 2, the injection system of the present disclosure can be used to advance the puncture element through a first region 211 and inject the injection agent into a second region 212 that produces a smaller opposing force to the injection than the first region. In some embodiments, less force may be required to inject the injection agent into the second region than the first region. In some embodiments, the density of the first region may be higher than the density of the second region, so that it may be easier to inject the injection agent into the second region than the first region. In some embodiments, the first region exerts higher backpressure on the puncture element than the second region, such that there is more opposition or resistance to flow of the injection agent into the first region relative to the second region.

In reference to FIG. 2, in step 201, an embodiment of the injection system is illustrated in an initial position. The injection system includes an injection agent in the injection chamber 114, and the puncture element is exposed and extends slightly beyond the distal tip 106 of the syringe barrel. In step 202, the puncture element is pre-inserted into a first region (for example, tissue such as sclera of the eye). During the pre-insertion, the tip of the puncture element is inserted into the first region of the tissue (e.g. the sclera) such that at least the lumen of the puncture element is imbedded or blocked by contact. In some embodiments, this step can be accomplished manually by penetrating the sclera with the exposed length of the puncture element. In some embodiments, the need to able to pre-insert the puncture element into the first region may set a limit to the range of lumen diameter and bevel size of the puncture element that can be used effectively to target the SCS. For example, the density of the first region may be a factor when selecting an appropriate puncture element. In some embodiments, the puncture element can be inserted tangentially to the sclera with the puncture element tip pointing to the posterior segment of the eye. Once the puncture element is pre-inserted into the first region, the lumen of the puncture element is blocked such that the injection agent can be conveyed through the puncture element.

In some embodiments, with a minimal human scleral thickness in mind, optimal results can be obtained by limiting the pre-insertion depth to less than or equal to approximately 0.5 millimeters (for example, between about 0.05 mm to 0.5 mm) if the puncture element is inserted perpendicular to the scleral surface. If the puncture element is pre-inserted at an angle other than perpendicular, one can sufficiently insert the puncture element with a longer bevel without piercing through the sclera. In some embodiments, the puncture element may have a bevel length less than 2 mm, less than 1 mm or less than 0.5 mm. The bevel angle can be greater than 15 degrees, greater than 30 degrees, or even greater than 45 degrees. For example, based on geometrical correlation, a 30-gauge puncture element with the standard bevel (angle: 12 degrees, length: 1.45 mm) inserted at an angle less than or equal to approximately 20° to the surface will reach less than 0.5 millimeters deep when measured normally from the surface. Similarly, larger puncture elements with longer bevel lengths can also be used. Shorter bevels allow for a greater range in angles of pre-insertion for a given puncture element size. Broadly speaking, puncture elements with outer diameters smaller than the scleral thickness of approximately 0.5 millimeters are readily usable to access the SCS and the angle of puncture element insertion is determined based on the beveled tip length.

In step 203, a force is applied on the pushing sealing element in the distal direction to advance the pushing sealing element in the distal direction. In some embodiments, the pushing sealing element advances with sliding motion or rotating motion (e.g. screw). The movement of the pushing sealing element applies a force on the injection agent, which pressurizes the injection agent, and the floating sealing element in the distal direction. In the first region, the frictional forces between the floating sealing element and the syringe barrel are less than the force necessary to inject the injection agent into the first region. As such, in the first region, the force applied on the pushing sealing element is sufficient to overcome the frictional forces between the floating sealing element, but is insufficient to inject the injection agent into the first region. Accordingly, in step 203, the force applied on the pushing sealing element causes the floating sealing element and thus the puncture element to advance in the distal direction deeper into the first region, without conveying the inject agent from the injection chamber.

In step 204, the puncture element reaches the interface between the first region and the second region such that the lumen of the puncture element partially or fully opens into the second region to fluidly connect the second region with the injection chamber. The force opposing the flow of the injection agent into the second region is less than that of the first region. Thus, the force needed to inject the injection agent into the second region is less than the frictional forces between the floating sealing element and the syringe barrel. In this manner, when the lumen of the puncture element accesses the second region, the floating sealing element automatically stops thus limiting the depth the puncture element penetrates into the cavity.

In step 205, because the force needed for the injection of the injection agent into the second region is less than the frictional force on the floating sealing element, the force on the pushing sealing element causes the injection agent to be injected into the second region, while the floating sealing element remains stationary. The puncture element does not penetrate further into the second region, but essentially holds its position at the interface between the first and second region. In some embodiments, the vector of fluid flow is parallel to the suprachoroidal space to provide broad coverage of the posterior segment of the eye instead of the fluid force being used to displace the choroidal and retinal tissues radially.

By way of non-limiting example, backpressure or opposing force experienced by the pushing sealing element is a function of the pushing sealing element speed and puncture element size. In some embodiments, such force can be in the range of 2 to 100N. In some embodiments, such force can be between 2 and 50N. By way of a non-limiting example, for a 30 G puncture element, 1 ml syringe, when the pushing sealing element is pushed at 0.5 mm/s, force experienced by the pushing sealing element to inject in sclera is about 5-20 N. Injecting in the SCS is closer to injecting in open air, ranging between 0 to 2 N for the same set of parameters.

In some embodiments, the force on the first sealing element can be greater than 2N (depending on the syringe barrel ID/puncture element ID ratio) in the first region and less than 1N in the second region. Accordingly, the max force that can be applied to move the puncture element distally, without releasing the injection fluid is more than 2N in the first region (for example, sclera) and less than 1 N in the second region (for example, SCS). It should be noted that, in the first region, the force on the second sealing element is less than the force it takes to inject the injection fluid into the first region. In some embodiments, as the injection agent exits the puncture element, it applies a force on the puncture element and the first sealing element, which increases with a higher flow rate. When the flow rate increases over a threshold value, the puncture element is pushed forward. To prevent, the movement of the puncture element, the max threshold flow rate can be increased by increasing friction on the first sealing element. As described below, the present disclosure also provides other means for arresting the distal movement of the first sealing element and the puncture element once the second region is reached. Additional non-limiting examples of acceptable forces and flow rates are disclosed in Nat Biomed Eng. 2019 August; 3(8): 621-631, incorporated herein by reference in its entirety.

Referring back to FIG. 2, once the puncture element reaches the interface between the first and second regions, the opposing force on the injection agent falls, so that, as the operator continues to push on the pushing sealing element, the injection agent in the injection chamber is delivered into the second region, while the puncture element holds its position at the interface between the first and second regions. While the floating sealing element can travel the full length of the syringe (i.e. millimeter distances), it can stop with micron level precision once the puncture element reaches the interface between the regions. This allows for therapeutic agent to be targeted and delivered primarily, and in some instances, only, in the thin "cavity" section of the anatomy, and not in the "tissue" section of the anatomy, as shown in FIG. 2. In some embodiments, the injection system of the present disclosure is configured so that, when the lumen of the puncture element opens into the second region, the floating sealing element and the puncture element can stop within a length of 250 microns, 200 microns, 150 microns, 100 microns, 50 microns, 25 micron upon entering the second region.

In some embodiments, the puncture element can travel through the first region as a constant speed so that a quasi-static equilibrium can be assumed, indicating that the forward and backward forces are balanced. As the needle enters the second region (cavity/space), there is immediate reduction in the backward force. The stopping distance can thus be directly related to the deceleration of the puncture element and its original speed of travel. Typically, the speed of travel would be low (0.1 mm/s to 10 mm/s, depending on the puncture element diameter). The deceleration is a function of the forward force applied on the sealing elements and the puncture element (the driving or pushing force) and backward force applied by the friction between the seal and the barrel. Assuming the friction stays relatively constant for a given design, deceleration will be dependent on the driving force which is related to the geometry of the puncture element and fluid viscosity. At the completion of the injection, the pushing sealing element comes in direct contacts with the floating sealing element. This can move the puncture element forward which is a safety concern. The present disclosure provides various safety features that can ensure that once the puncture element stops as described above, it will maintain the position even when the pushing sealing element makes contact with the floating sealing element.

In some embodiments, the first region may correspond to a tissue of a patient and the second region may correspond to a space or potential space in the tissue or adjacent to the tissue. In other words, the injection system 100 of the present disclosure can be used to advance the puncture element 116 through a tissue of a patient (for example, sclera of the eye) and to inject the injection agent into a space or potential space adjacent to the tissue (for example, the suprachoroidal space or the intracameral space). The term "space" includes an actual space or cavity or a potential space in tissue. The potential space refers to a space that is collapsed under typical physiological conditions (e.g., multiple tissue in contact with one another), but has a potential to expand when forced open (e.g. in response to a fluid injection). For example, the suprachoroidal space (SCS) is a potential space between the sclera and choroid that traverses the circumference of the posterior segment of the eye. In some embodiments, the injection system of the present disclosure is capable of delivering drug and gene therapies that benefit from localization to the SCS including those that treat diseases and disorders of the choroid and the retina. Disclosed herein are various embodiments that enhance the ability of the injection system to target SCS and deliver injection agent of interest to the tissues in posterior segment of the eye (for example, retina, retinal pigment epithelium, Bruch's membrane, choroid). Successful injections that accurately and consistently target the SCS by penetrating through the sclera can deliver various classes of therapeutics to the choroid. Between the SCS and the retinal pigment epithelium lays Bruch's membrane, which serves as a diffusion barrier to injection agents delivered via the SCS reaching the retina. Moore et al. (2001) reports that the permeability of Bruch's membranes isolated from donated human eyes ex vivo decreased with age. While the Bruch's membranes of young donors showed permeability to proteins greater than 200 kDa, older donors showed decreased permeability. The Bruch's membranes of older donors continued to show permeability to proteins greater than 100 kDa. It should be noted, however, that while the present disclosure describes the injection system in connection with drug delivery to the SCS cavity, the presently disclosed systems and methods can be used to deliver injection agents to other voids or cavity of the human body, or in other applications outside the human body. For example, the injection system of the present disclosure can be used for injection into pericardial membrane, pleural cavity (potential space between the two pleurae (visceral-parietal) of the lungs), synovial cavity between joints, space between scar tissue and implant (e.g. scar tissue around breast implant to treat capsular contracture, airway access, vascular access and similar biological spaces or potential spaces.

In some embodiments, it may be desirable to prevent the proximal movement of the floating sealing element during the initial insertion of the puncture element into the tissue. In particular, the syringe barrel, the pushing sealing element, and the floating sealing element of the injection system may be configured, individually or in combination, to avoid backwards (proximal) movement of the floating sealing element past a pre-selected location. In some embodiments, the injection system of the present disclosure may be used to deliver injection agents that are expensive and that need to be administered with precise doses. In some embodiments, such dosage may be within 10% of the labeled volume. Accordingly, in some embodiments, the injection system may include one or more features that ensure that the entire or substantially entire volume of the injection agent is administered to the patient. In some embodiments, these two features are combined. In some embodiments, the syringe barrel, the pushing sealing element, and the floating sealing element of the injection system may be configured, individually or in combination, to avoid backwards (proximal) movement of the floating sealing element past a pre-selected location, while allowing the pushing sealing element to come in contact with the floating sealing element to minimize or eliminate the dead volume between the sealing elements. In some embodiments, such design may ensure that all or substantially all of the therapeutic payload is delivered to the patient.

In reference to FIG. 3, in some embodiments, an injection system of the present disclosure may include a one-way stop 210 that is configured to prevent backwards movement of the floating sealing element, for example, during the pre-insertion of the puncture element into the tissue. In some embodiments, the one-way stop 210 is located and configured such that the pre-insertion of the puncture element is achieved without the floating sealing element traveling backwards and causing loss of more than 10% of the injection volume of the therapeutic agent.

In some embodiments, the one-way stop can prevent the pushing sealing element from moving past the stop. In some embodiments, the one-way stop can also be configured to allow the pushing sealing element to pass unimpeded. In this manner, at the end of the injection, the gap between the pushing sealing element and the floating sealing element can be reduced or eliminated to enable the full therapeutic fluid payload to be injected into the cavity and reduce or eliminate dead volume. In some embodiments, the distal side of the pushing sealing element is allowed to substantially come in contact with or touch the proximal side of the floating sealing element, such that there is de minimis dead volume between the sealing elements. In some embodiments, another one-way stop may also be provided proximal to the pushing sealing element to prevent the proximal movement of the pushing sealing past a desired point.

In some embodiments, the one-way stop 210 may be provided directly proximal to (that is, behind) the floating sealing element. In this manner, after the initial set-up, the floating sealing element is prevented from being able to travel proximally past the one-way stop. In some embodiments, in the initial set-up, the tip of puncture element is sufficiently exposed to allow for blocking of the lumen when the puncture element is pre-inserted into the tissue, which is dependent on the bevel angle. Depending on the puncture element size and bevel angle, this length could change. In some embodiments, in the initial set-up, the puncture element tip is exposed by 0.2 mm to 2 mm. In some embodiments, when the floating sealing element is in the initial set-up, about 0.5 mm of the puncture element is exposed. In some embodiments, the puncture element tip may be exposed more than the scleral length, and so, the puncture element may be inserted into the sclera at an angle, instead of normal to the surface.

Figure 4:
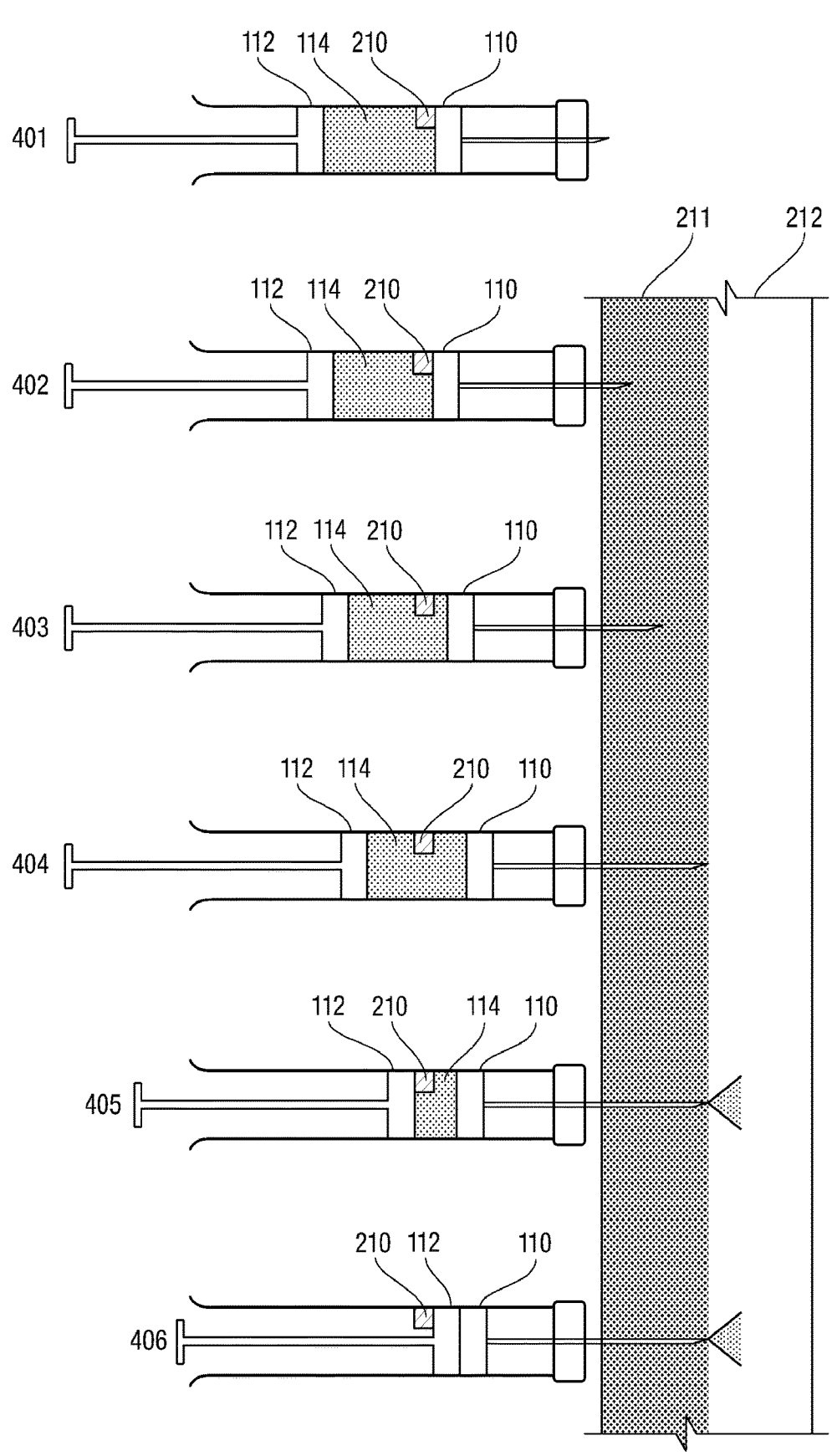
FIG. 4 illustrates an exemplary method of use of an embodiment of an injection system of the present disclosure having a one-way stop.

The operation of an injection system with a one-way stop is shown in FIG. 4. The injection system of the present disclosure with the one-way stop 210 operates essentially the same as described in connection with FIG. 2. The one-way stop 210 can ensure that the floating sealing element 110 is not pushed backwards when the puncture element is first inserted into the tissue. On the other hand, the one-way stop 210 is designed such that the pushing sealing element 112 can pass through the one way stop to come in contact with the floating sealing element at the end of the injection. In this manner, all or substantially all of the injection agent can be delivered into the target space.

In reference to FIGS. 5A and 5B, in some embodiments, the injection system 100 of the present disclosure comprises a reduction 310 in diameter of the syringe barrel at one or more locations. In some embodiments, the reduction 310 may be provided proximal to the floating sealing element 110 as a one-way stop. In some embodiments, the inner diameter of the syringe barrel may be reduced to create the one-way stop at a pre-selected position between the pushing sealing element and the floating sealing element. In some embodiments, the reduction in the diameter provides sufficient resistance to back-pressure during the pre-insertion of the puncture element into the issue, so as to avoid the backward movement by the floating sealing element. Yet, the reduced inner diameter is sufficiently large and/or the pushing sealing element is configured, so that the pushing sealing element can travel past that region with relative ease to meet the floating sealing element, thus enabling the user to fully dispense the therapeutic fluid, reducing both dead volume and injection volume variability. For example, the pushing sealing element may be made of a softer material than the floating sealing element to allow the pushing sealing element to be squeezed by the reduction in the diameter of the syringe barrel. In some embodiments, additionally or alternatively, there may be a reduction in the syringe barrel diameter proximal the pushing sealing element.

In some embodiments, the diameter of the syringe barrel can be reduced by crimping or pinching the syringe barrel, for example, at a desired location proximally to the floating sealing element. In some embodiments, the syringe may be molded to include a mechanical stop inside the lumen of the syringe barrel, thereby reducing the diameter at that location. In some embodiments, the inner diameter of the syringe barrel can be reduced by modifying the inner surface of the syringe barrel, such as, for example, by including one or more projections, ridges or flanges on the inner surface of the syringe barrel. In some embodiments, the syringe barrel may have a variable diameter along its length, with a larger diameter in the distal section to house the floating sealing element and a smaller diameter proximal to the floating sealing element to prevent the floating sealing element from traveling too far backwards.

In reference to FIGS. 6A and 6B, in some embodiments in the injection system of the present disclosure, the one-way stop may be provided by modifying the floating sealing element 110 to have a shape that results in asymmetric sliding forces acting on the floating sealing element 110 during its movement. For example, due to such shape modifications, the floating sealing element can experience a much higher friction when moving in the proximal direction than when moving in the distal direction. In this way, the floating sealing element can easily travel in the distal direction from its initial position but can be prevented from traveling in the proximal position. On the other hand, the pushing sealing element is free to travel towards to and up to the floating sealing element without any impediments or obstacles. In some embodiments, the design of the floating sealing element is unique in that it only allows for unidirectional motion, as compared to bidirectional motions of conventional syringe plungers. In some embodiments, as shown in FIG. 6A, the floating sealing element includes a series of specialized ridges that have steeper angles facing the back of the floating sealing element than the angles facing the front portion of the pushing sealing element. For example, the floating sealing element can comprise one or more conical frustums or barbs facing in the distal direction. Such designs can promote the forward motion of the floating sealing element, relative to the backward motion. In some embodiments, the interior of the syringe barrel contains barbs that are angled towards the proximal direction. In some embodiments the interior of the syringe barrel can contain ribs, ridges, toroidal shapes or similar shapes angled or flattened in the proximal direction. In some embodiments, similar modifications may be made to the pushing sealing element and/or in the syringe barrel proximal to the pushing floating element.

In some embodiments, the frictional forces between the floating sealing element and the inner surface of the syringe barrel can be adjusted (increased or decreased) by materials selection (e.g. polytetrafluoroethylene, polyethylenes, polypropylenes, thermoplastic elastomers, fluroelastomer—all of which can be siliconized or non-siliconized), number of angled directional ribs or thickness of ribs to address the viscosity of the formulation. In some embodiments, the frictional force on the floating sealing element can be decreased by using a polytetrafluorethylene surface.

Figures 7A, 7B, 7C, 7D, 7E:
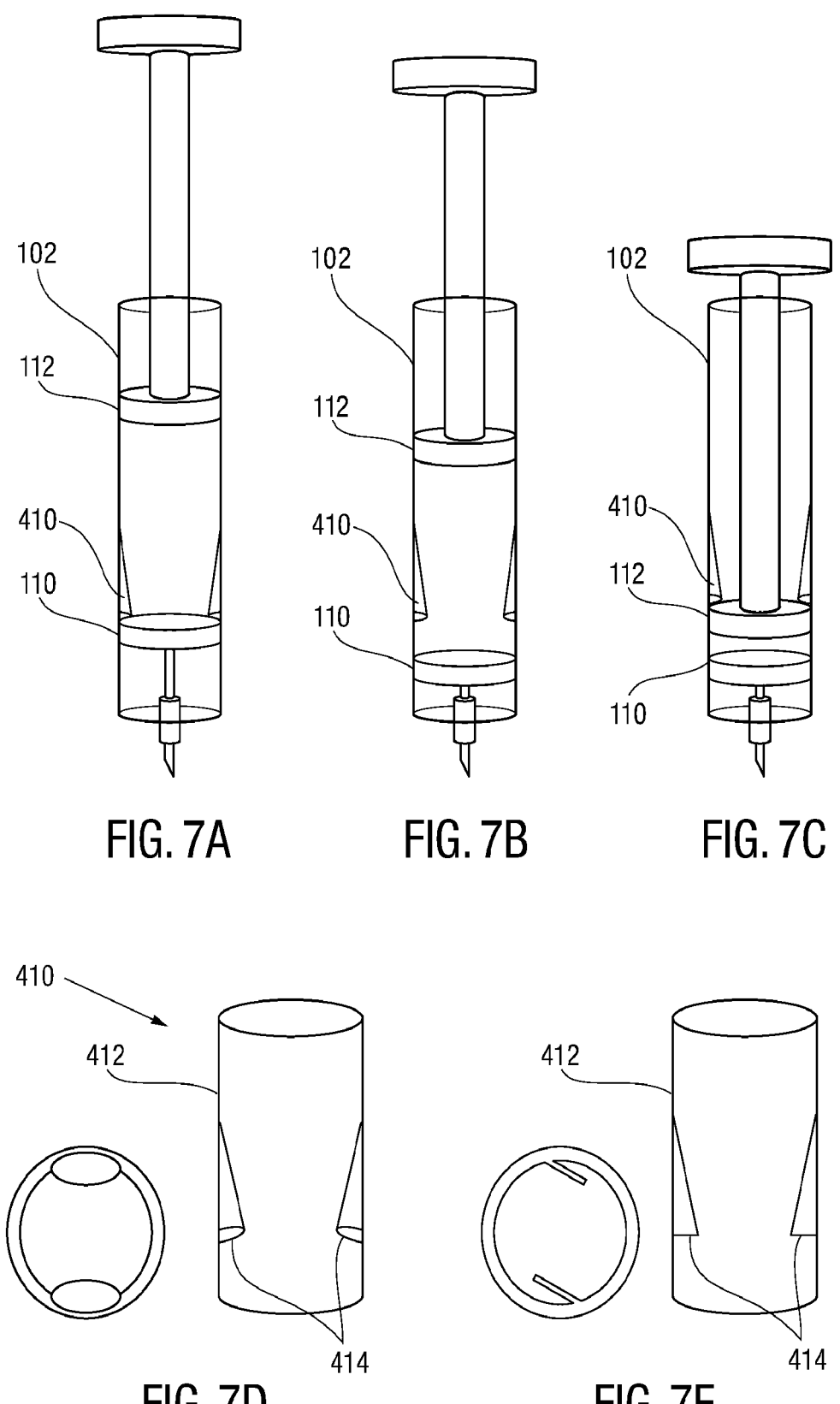
FIGS. 7A-7C show an embodiment of an injection system of the present disclosure with a foldable one-way stop.
FIGS. 7D-7E show various embodiments of a folding one-way stop suitable for use in an injection system of the present disclosure.

In reference to FIGS. 7A, 7B and 7C, in some embodiments, the one-way stop may comprise a foldable one-way stop 410 disposed within the syringe barrel 102. Similar to the one-way stops described above, placing foldable stops into the inner aspect of the syringe barrel creates a one-way stop disallowing the floating sealing element from backward motion during pre-insertion, while allowing the pushing sealing element to advance past the foldable stop by folding the foldable stop down during dispensing of the injection agent. In some embodiments, the foldable one-way stop may be provided as an insert for the syringe barrel. In reference to FIGS. 7D and 7E, such foldable stop 410 can include a body 412 with one or more foldable gates 414 that can only be folded by an application of force in the distal direction. In some embodiments, the floating sealing element may be situated against the foldable stop. During the puncture element insertion, the floating sealing element may be pushed backward in the proximal direction, but it will be held in place by the foldable stop. In some embodiments, the floating sealing element is rigidly connected to the folding stop, so that there is minimal compliance when the floating sealing element is pushed backwards by the insertion forces. However, during the administration of the injection agent, when the pushing sealing element reaches the foldable stop, the pushing sealing element applies a force on the gates in the distal direction, thus causing the gates to fold away and allowing the pushing sealing element to pass through the foldable stop toward the floating sealing element. In some embodiments, an insert with a foldable stop may be proved in the syringe barrel.

Figures 8A, 8B, 8C, 8D:
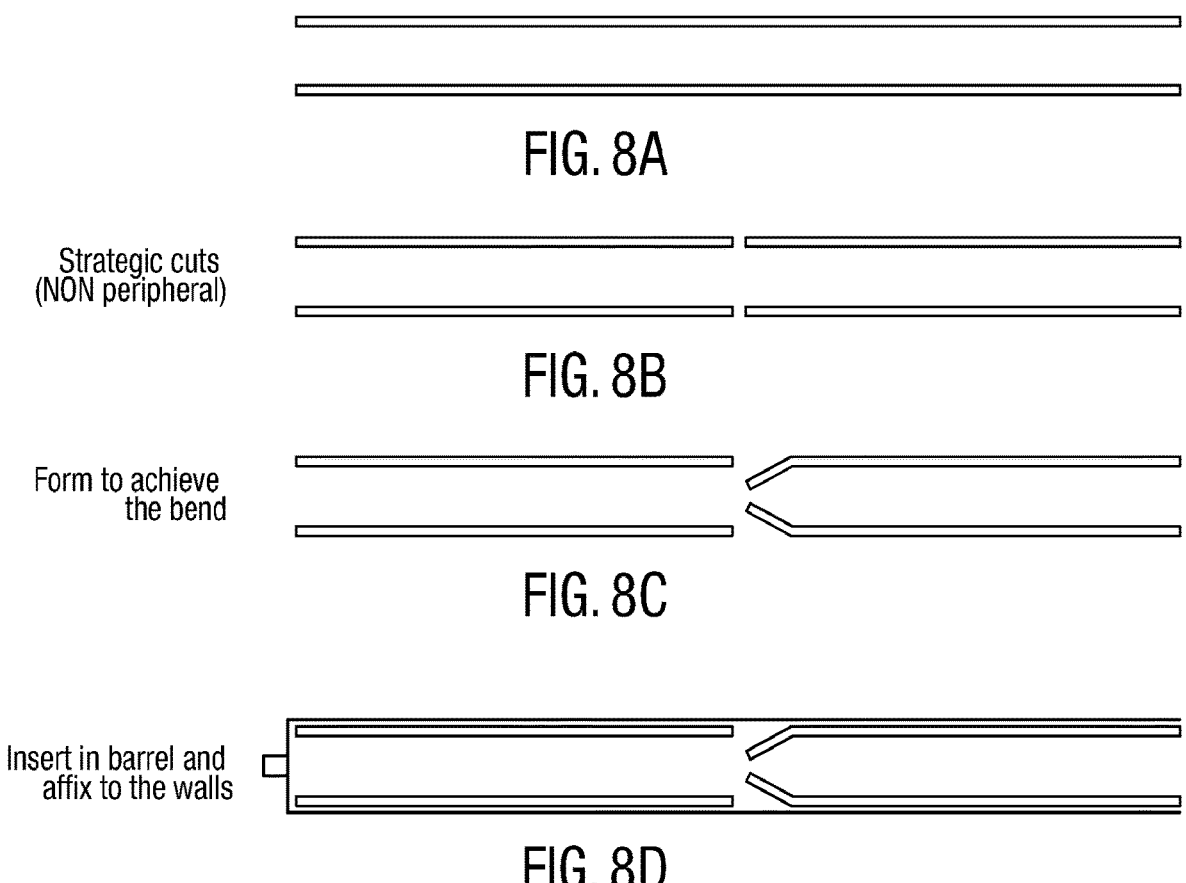
FIGS. 8A-8D illustrate an exemplary process of manu-facturing an injection system with a foldable one-way stop.

FIGS. 8A-8D provide an exemplary process for manufacturing a syringe including a one-way foldable stop. For example, FIG. 8A shows a hollow tube sized to snuggly fit inside a syringe of choice. Strategic non-peripheral cuts are made to create foldable gates as shown in FIG. 8B. These flaps are then formed to a desired shape as exemplified in FIG. 8C. This structure can then be inserted in a syringe barrel as shown in FIG. 8D. This structure may be adhesively bonded, welded, mechanically fastened to the syringe barrel, if necessary.

Additionally or alternatively to a one-way stop and/or the change in the frictional force between the floating sealing element and the syringe barrel, in some embodiments, the contents of the syringe barrel (e.g., the injection agent in the injection chamber) can be pressurized prior to pre-inserting the puncture element into the tissue to prevent the proximal travel of the floating sealing element during the pre-insertion step. In some embodiments, the user can apply pressure to the pushing sealing element, but preferably not so much pressure as to move the floating sealing element. In some embodiments, the pushing rod can be momentarily locked in position (with a linear actuator, for example) to fix the position of the pushing sealing element so as not to move the floating sealing element during the pre-insertion step. In some embodiments, the puncture element may be provided with a plug to keep it from leaking when the syringe barrel is pressurized. Such plug may allow the puncture element to travel as the pushing sealing element is pushed until the plug makes contact with the tissue. In some embodiments, the plug can be configured to allow the puncture element to pierce through the plug for pre-insertion into the tissue, while the plug contacts the tissue with sufficient force to form a fluid-tight seal with the tissue. In some embodiments, the plug is made of a material that can be pierced by the puncture element, while making a seal with the tissue around the pre-insertion site.

In some embodiments, the injection system of the present disclosure is designed such that the frictional resistance/ force between the syringe barrel and the pushing sealing element, the floating sealing element, or both can be greater than the insertion force required to penetrate into the sclera. In some embodiments, the frictional resistance can be increased by modifying the inner surface of the syringe barrel or modifying the size or shape of the sealing elements, or using materials with higher friction, as described elsewhere in the application, for example, in connection with the embodiments for higher viscosity injection agents shown in FIG. 14. In this manner, the puncture element can be pre-inserted into the tissue (sclera) without the floating sealing element traveling backwards. In some embodiments, the frictional resistance of the floating sealing element may be higher than the force needed to inject a cavity for a particular formulation viscosity, syringe barrel inner diameter and puncture element inner diameter so that when the floating sealing element auto-stops at a cavity, pressing the pushing sealing element to express the injection agent at the syringe tip does not cause the puncture element to further advance. In other words, the frictional resistance of the floating sealing element can also be higher than the force applied to the pushing sealing element to inject into a cavity for a particular formulation viscosity, syringe barrel inner diameter and puncture element inner diameter. In this manner, the floating sealing element can auto-stop at a cavity and pressing the pushing sealing element to express the injection agent at the syringe tip will not cause the puncture element to further advance.

In such a design, the user can have a haptic feedback when the floating sealing element auto-stops and the injection agent is at the puncture element tip in the cavity. In some embodiments, the haptic feedback is based upon the feeling of loss of resistance at pushing sealing element. In some embodiments, the haptic feedback can be used in combination with the visual feedback of the floating sealing element stopping to determine when the delivery of the therapeutic fluid commences. In some embodiments, in regard to the visual feedback, for example, if the pushing sealing element continues to move while the floating sealing element is not moving and no visible leak on the tissue surface are observed, it is a strong indicator that the puncture element is delivering the injection agent at the desired location.

Figures 9A, 9B, 10A, 10B:
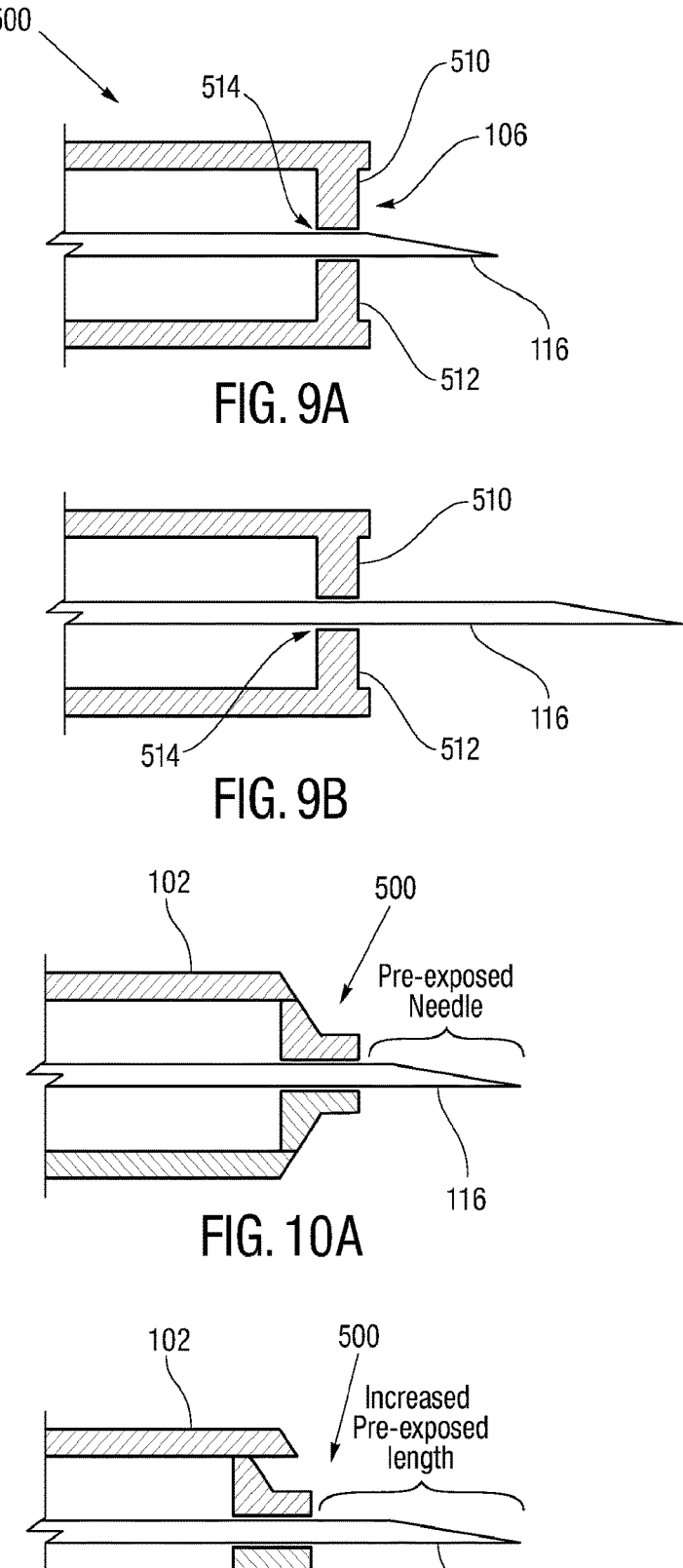
FIGS. 9A-9B show various embodiments of a distal end of an injection system of the present disclosure with a needle support.
FIGS. 10A-10B show various embodiments of a distal end of an injection system of the present disclosure with a needle support.

In some embodiments, the injection system of the present disclosure is miniaturized to deliver about 100 to 250 microliter volumes with a precision of ±10% with a long thin gauge puncture element that penetrates the stiff scleral tissues. In some embodiments, the precision may be increased to ±5%. The size of the syringe may be 10 ul to 50 mL FIGS. 9A and 9B illustrate an embodiment of the distal end 106 of the injection system. In some embodiments, a puncture element support 500 can be provided at the distal end of the syringe barrel to support the puncture element. Such slidable support may be stationary or slidable relative to the syringe barrel. In some embodiments, the slidable support 500 may comprise support flanges 510, 512 that may be disposed near the distal end of the syringe barrel. The support flanges 510, 512 are spaced apart from one another to provide an orifice 514 that enables the puncture element 116 to slide between the support flanges. At the same time, the support flanges 510, 512 can provide support to the puncture element near the tip to reduce puncture element movement caused by bending of puncture element while penetrating sclera and altering forces on the floating sealing element. In some embodiments, the flanges 510, 512 may be integral with the syringe barrel.

In some embodiments, the puncture element support contacts the sclera. In some embodiments, the puncture element support can be beveled to allow for injection at an angle to the surface of the sclera. In some embodiments, the pre-insertion angle is 45 degrees or greater from the perpendicular plane. In some embodiments, the surface of the puncture element support contacting the sclera can be serrated to partially penetrate the sclera. In this manner, the puncture element support can firmly grasp the sclera to avoid any unwanted scleral movement. The orifice of the slidable puncture element can be sized to accommodate size and shape of puncture element employed.

In some embodiments of the injection system, the puncture element is exposed only a short distance (100 um to 5 mm) such that the puncture element does not pierce entirely through sclera but may extend further while performing SCS delivery while the floating sealing element is activated. In some embodiments, puncture element support can contact the surface of the sclera before the puncture element, with the puncture element and slightly after the puncture element.

In reference to FIGS. 10A and 10B, the puncture element support may be slidably disposed in the syringe barrel, so that the exposed length of the puncture element can be adjusted prior to performing SCS delivery. In some embodiments, the distal face of the puncture element support can be orthogonal with the central axis of the syringe barrel or at angle. In some embodiments, the pre-exposed length of the puncture element may be adjusted prior to pre-insertion, which can be independent of the floating sealing element. For example, FIG. 10B shows that the puncture support element may be moved in the proximal direction to increase the exposed length of the puncture element compared to when the puncture support element is set more distally in the syringe barrel as shown in FIG. 10A. However, as the puncture element is pre-inserted into the eye of the patient, the length of the puncture element penetration can still be controlled by the movement of the floating sealing element. The operator may feel the difference in force needed to be applied on the pushing sealing element if the pushing sealing element is pushed manually. The puncture element stops and immediately starts delivery of the injection agent payload without the need for the user/physician to change their action (e.g., they continue to push the pushing sealing element).

Figure 11A:
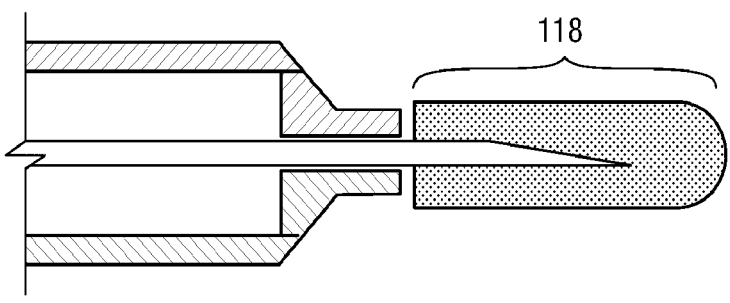
FIGS. 11A-11C show various embodiments of a safety cap suitable for use with an injection system of the present disclosure.
Figure 11B:
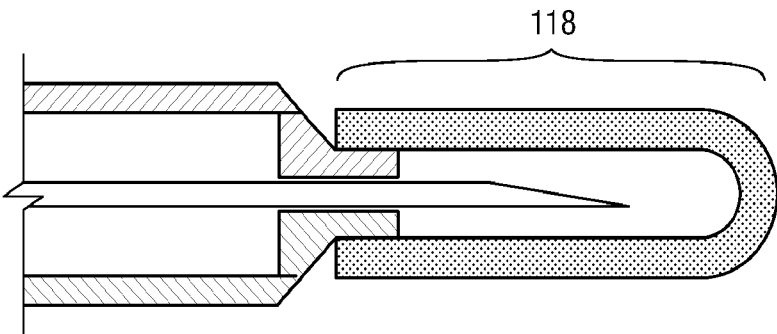
Figure 11C:
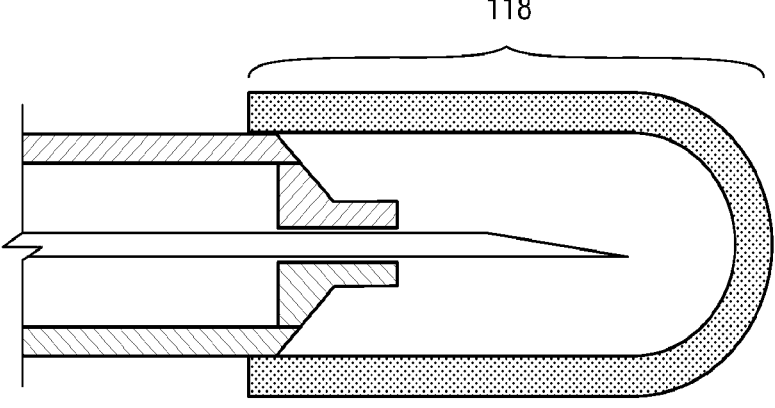

In reference to FIGS. 11A-11C, various embodiments of the safety cap 118 are shown. The safety cap can protect the puncture element from mechanical damage before use. In some embodiments, the safety cap can also seal the puncture element to ensure that the injection agent does not leak or get injected from the injection chamber during storage. The lid may be secured on the syringe using frictional force, interlock, or threads.

In reference to FIGS. to 12A-12E, in some embodiments, the injection agent may be provided as multiple components that can be stored separately within the injection chamber and can be mixed immediately prior to the use of the injection system to deliver the injection agent to the target. In some embodiments, an injection agent can be stored separately within the injection chamber, separated from its diluent. On applying pressure, the diluent is mixed with the therapeutic to create a solution or suspension, which can then be injected into the SCS. In some embodiments, the therapeutic may be lyophilized therapeutic.

In some embodiments, the injection system may have multiple chambers such that the chambers are isolated from each other. In some embodiments, the injection agent may include a dry component stored in one chamber and a diluent stored in another chamber. In use, the diluent may be forced from its chamber into the chamber with the dry component, which accomplishes the in-situ reconstitution of two components of the formulation for injection.

Figure 12A:
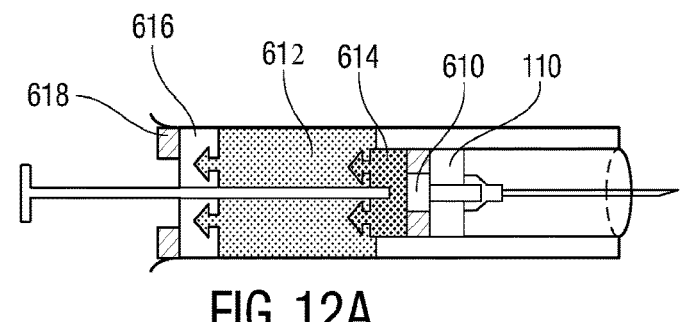
FIGS. 12A-12E show an embodiment of an injection system of the present disclosure prefilled with a multi-component injection agent.
Figure 12B:
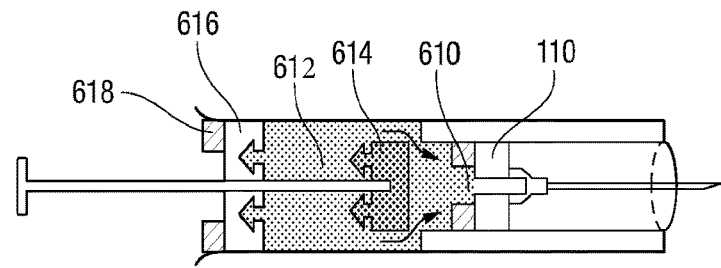
Figure 12C:
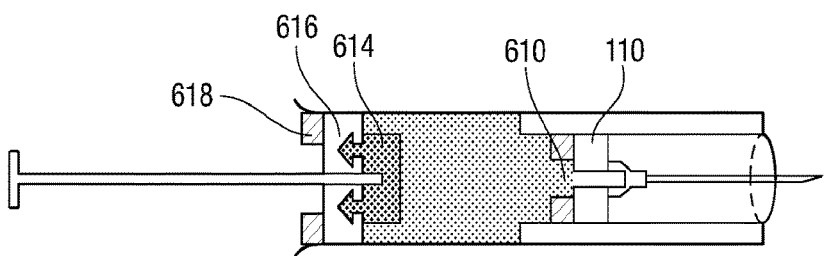
Figure 12D:
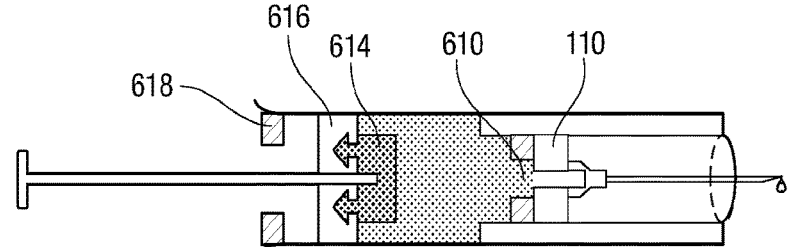
Figure 12E:
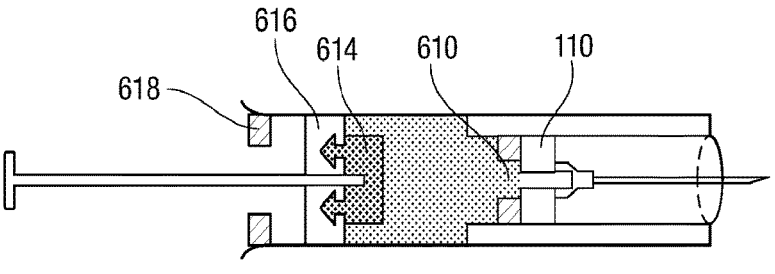

As shown in FIG. 12A, in some embodiments, the two chambers 610, 612 are initially separated by the rubber (or other material) seal 614 mounted on the floating sealing element. The chamber 610 may be defined by the seal 614 and the floating sealing element 110, while the chamber 612 may be defined by the seal 614 and a back seal 616 of the pushing sealing element 112. In some embodiments, there may be flutes in the inside wall of the syringe barrel that connect the two chambers when the seal is moved in one direction. In some embodiments, the chamber 610 contains lyophilized active substance of the therapeutics, while the chamber 612 contains a carrier injection agent that can be used to reconstitute the active substance. A one-way stopper 618 may be disposed proximal to the back seal 616 of the pushing sealing element such that the back seal 616 may move forward but cannot move back. As the seal 614 is moved back, the fluid inside the chamber 612 gets pressurized. At the same time, the movement of the seal 614 connects the two chambers, as shown in FIG. 12B. Pressurized fluid from the chamber 612 now enters the chamber 610 and mixes with the contents in the chamber 610. The seal 614 may be moved back and forth to enable efficient mixing of the two components. As the seal is fully extended back, the seal engages with the back seal of the pushing sealing element such that both the seals now move together, as shown in FIG. 12C. In some embodiments, the seals may be provided with corresponding anchors and anchoring ports. Now a force can be applied on the pushing sealing element to operate the injection system. The injection system can now be primed, as shown in FIG. 12D, so it is ready for use, as shown in FIG. 12E.

The mechanism engaging the seal 614 and the back seal 616 may be mechanical, adhesive, or magnetic. In some embodiments, it is shown as a mechanical anchor. In some embodiments, the therapeutic solution or suspension is stored pre-filled in the system for injection. In some embodiments, the therapeutic is stored either as a ready-to-use solution, or as a lyophilized powder requiring reconstitution, in one or more vials that comprise a kit. In these embodiments, the therapeutic, either ready-to-use, or reconstituted, is loaded into the system for delivery and then injected into the SCS.

Figure 13:
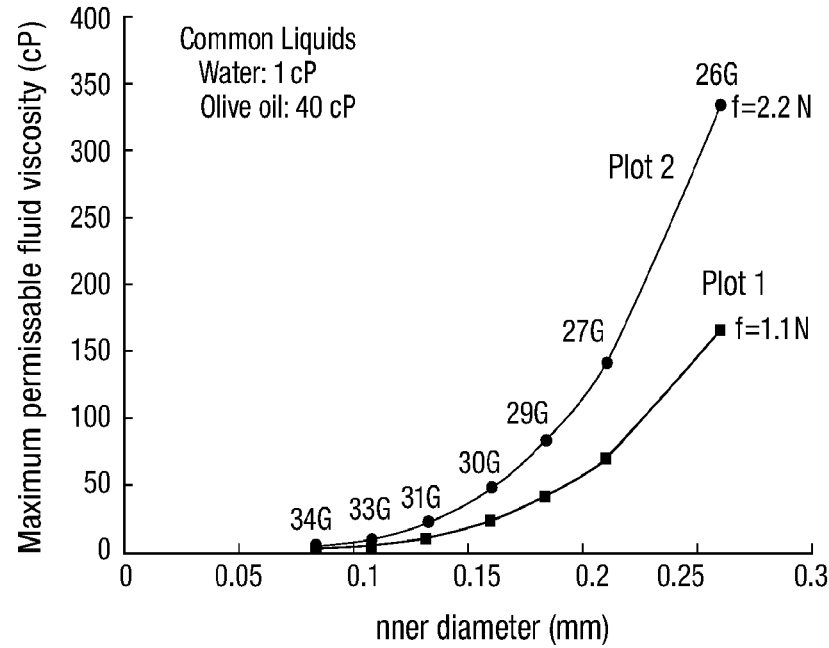
FIG. 13 shows a graph of an injection fluid viscosity as a function of an inner diameter of a puncture element in an injection system of the present disclosure.

In some embodiments, as noted above, the injection system of the present disclosure may be used to deliver injection agents with high viscosity, greater than 10 centipoise (cP). In some embodiments, the ability to deliver high viscosity therapeutics can depend on multiple parameters, such as, for example, puncture element length, puncture element lumen diameter and cross-sectional area, fluid density, syringe size, frictional and sliding force between the floating sealing element and the syringe barrel, and minimum flow rate. For example, in reference to FIG. 13, for a standard plastic 1 ml syringe/sealing element combination, with a minimum flow rate of 100 ul/min, the maximum viscosity as a function of puncture element gauge is plotted in Plot 1. In some embodiments, by increasing the frictional force between the floating sealing element and the syringe barrel, the maximum viscosity that can be injected for a given size puncture element can be increased as shown in Plot 2. For example, to generate the data for Plot 1, the frictional force between the floating sealing element and the syringe barrel was doubled. In some embodiments, a viscosity modifying agent can be added into the carrier fluid for the therapeutic solution or suspension, so that the haptic feedback on the pushing sealing element is increased to the user to improve control over injection.

Figure 14:
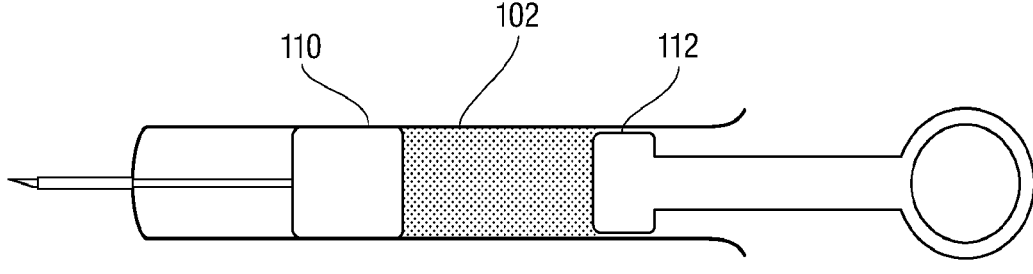
FIG. 14 shows an embodiment of an injection system of the present disclosure with an oversized sealing element.

In reference to FIG. 14, the injection system of the present disclosure includes a syringe barrel with an inner diameter that is under-sized relative to the floating sealing element diameter to increase the frictional force on the floating sealing element. In general, the frictional force is a function both of the relative size (for example, diameters and/or length) of the floating sealing element and the inner surface of the syringe barrel, as well as the materials properties (elastic and bending moduli) of both the floating sealing element and the syringe barrel. By way of a non-limiting example, the frictional force for a 1 ml syringe was measured to be ~1N. Max allowable viscosity and frictional force are directly proportional. Hence to increase the allowable viscosity limit by 10-fold, the frictional force would need to be increased 10-fold. Even small changes in the relative sizes of the floating sealing element and the syringe barrel can change the normal force on the floating sealing element, which would enable the administration of the injection agents with high viscosity. In some embodiments, when no external forces are acting on the floating sealing element, that is, in its relaxed state, the first sealing element can have a size that is between 1.01 to 2 times larger than the site of the lumen of the syringe barrel. In some embodiments, in a relaxed state, the first sealing element has a size that is between 1.01 to 1.10 times larger than a size of the lumen of the syringe barrel. In some embodiments, in the relaxed state, the first sealing element can have a size that is between 1.01 to 1.4 times larger than the size of the lumen of the syringe barrel. In some embodiments, the diameter of the lumen of the syringe barrel may be reduced to increase the frictional forces between the floating sealing element and the syringe barrel.

In some embodiments, such frictional force on the floating sealing element may be sufficient to prevent the proximal movement of the floating sealing element during the puncture element pre-insertion stage. In other words, the increase in the frictional force on the floating sealing element can have 2 advantages: 1) it keeps the floating sealing element in place during pre-insertion and 2) it allows the user to deliver therapies with higher viscosities. In some embodiments, the frictional or sliding force between the floating sealing element and the syringe barrel can be increased to be above the pre-insertion force so that the floating sealing element remains in place during pre-insertion. The pre-insertion force can depend on the geometry of the puncture element. In some embodiments, a viscosity modifying agent is added to the injection agent to enable increased frictional or sliding force on the floating sealing element, while the auto-stop functionality remains intact. In some embodiments, increasing or decreasing surface roughness of the syringe barrel can allow for the increase or decrease in the frictional force between the floating sealing element and the syringe barrel to adjust for the viscosity of the injection agent.

In some embodiments, the relationship between the sizes of the floating sealing elements and the syringe barrel can be adjusted by increasing the diameter of the floating sealing element while keeping the inner diameter of the syringe barrel constant, decreasing the inner diameter of the syringe barrel while keeping the diameter of the floating sealing element constant, or a combination of these 2 options. In both cases, in some embodiments, the pushing sealing element is configured to pass through the syringe barrel to contact the floating sealing element to eliminate the dead volume between the sealing elements, as discussed above. In some embodiments, the pushing sealing element may be made from a softer material and/or a material that can decrease friction between the pushing sealing element and the syringe barrel. Additionally or alternatively, the rigid portion of the pushing sealing element can be undersized relative to the elastic portion as compared with the floating sealing element to allow the pushing sealing element to be easily advanced to the floating sealing element. In some embodiments, additionally or alternatively, the diameter or shape of the puncture element can be changed to enable the delivery of the high viscosity injection agents using the injection system of the present disclosure.

In some embodiments, the injection system of the present disclosure is equipped with one or more safety features to limit or control the depth that the puncture element can extend into the eye of the patient. In some embodiments, such features can limit the distance the floating sealing element can travel in the distal direction, so the puncture element cannot extend outside the SCS. In some embodiments, because the length that the puncture element needs to travel to reach the cavity interface will vary among the patients, such safety features need to be sufficiently flexible or adjustable, so the maximum puncture element insertion distance can be set specific to each procedure.

Figures 15A, 15B, 15C, 15D, 15E:
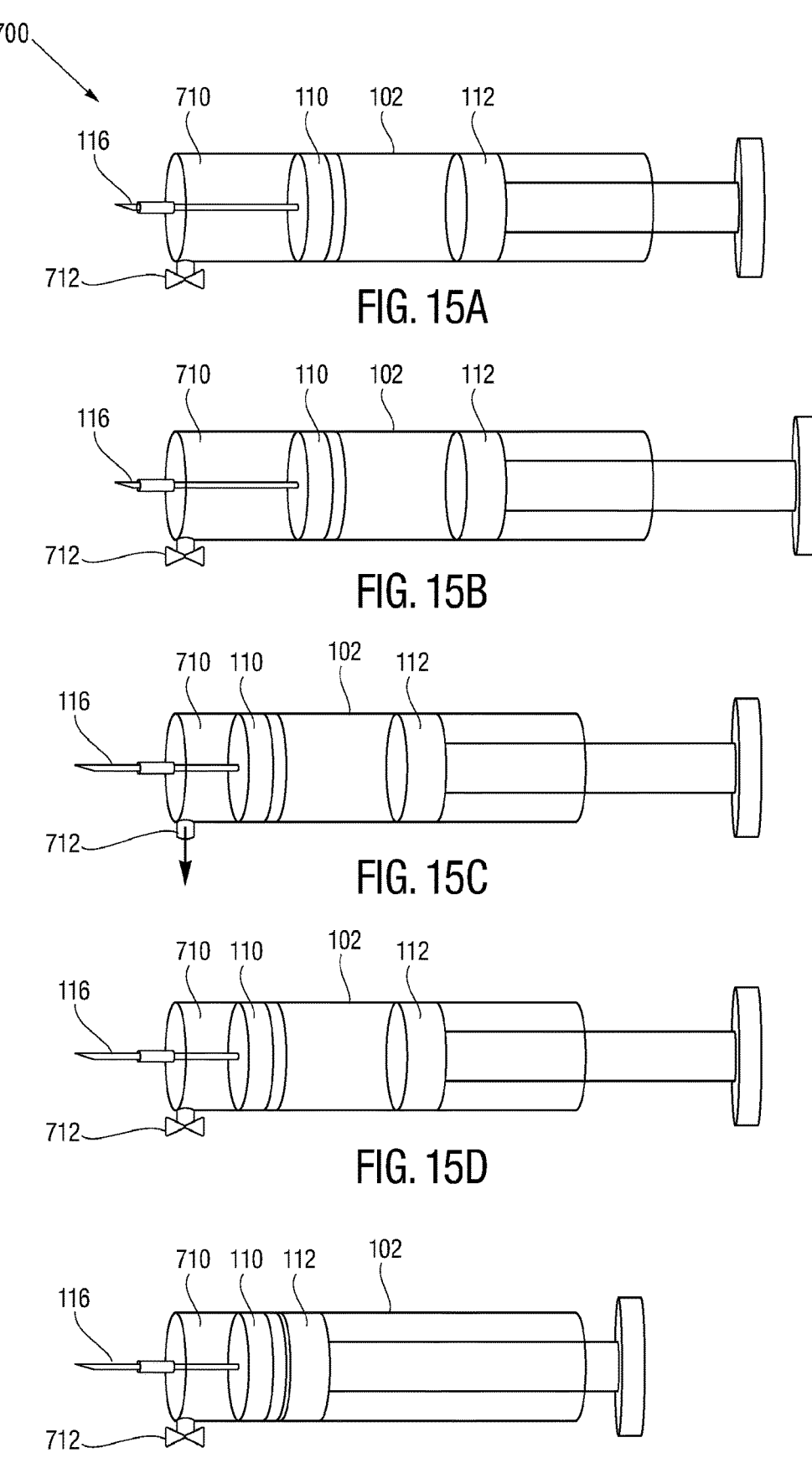
FIGS. 15A-15E show an embodiment of an injection system of the present disclosure having a lock for a sealing element.

In reference to FIG. 15A, in some embodiments, such safety feature may comprise a lock for selectively locking and unlocking the floating sealing element 110 in place. In some embodiments, the lock 700 comprises a sealed compartment in the distal region of the syringe barrel distally of the floating sealing element. The compartment 700 can be outfitted with a valve 712 (e.g. a ball valve, butterfly valve, pinch valve, control valve, gate valve, globe valve, or puncture element valve), so an incompressible substance, such as, for example, sterile fluid, liquid (e.g. sterile saline) or gas, can be let into or out of the compartment 710. Because the substance in the compartment is incompressible, the floating sealing element cannot move in the distal direction when the valve is closed. The valve can be a binary valve or a tunable valve. Opening the valve releases the incompressible substance from the compartment, so that the floating sealing element is allowed to move in the distal direction. To lock the floating sealing element again, the valve is closed.

The operation of the distal safety lock is illustrated in FIGS. 15B-15E. Prior to use of the injection system, the floating sealing element is placed in its desired initial position, the sealed compartment 710 can be filed with the incompressible substance and the valve 712 is closed to lock the floating sealing element at its initial location, as shown in FIG. 15B. The valve is kept closed during the syringe filling and puncture element pre-insertion steps, as applicable, to hold the floating sealing element in place. As shown in FIG. 15C, once the puncture element is preinserted into the tissue, the valve 712 can be opened to release a portion of the incompressible substance from the sealed compartment to enable the floating sealing element to move in the distal direction to advance the puncture element to the SCS interface. In some embodiments, a collection reservoir may be provided to collect the fluid released from the compartment. As shown in FIG. 15D, when the puncture element is positioned as desired for injection of the injection agent into the SCS (for example, at the interface of sclera and SCS), the valve is closed to lock the floating sealing element in place, which also ensures that the puncture element remains in the desired position. Because the remaining fluid in the compartment is incompressible, the floating sealing element cannot move in the distal direction when the valve is closed. The fluid lock can also prevent an overshoot by the puncture element by closing the valve after the puncture element reaches the SCS. For example, as shown in FIG. 15E, the fluid lock design would keep the floating sealing element stationary even when the pushing sealing element comes in contact with the floating sealing element, which can knock the floating sealing element forward or if the user accidently continues to push on the pushing sealing element.

In some embodiments, the viscosity of the incompressible substance used for the sealed compartment can be selected to counter-balance the viscosity of the injection agent. By increasing the viscosity of the fluid in the compartment, the amount of force necessary to expel the viscous fluid through the valve increases. This exerts additional resistance to the proximal movement of the floating sealing element, thereby increasing the sliding force of the floating sealing element.

Figure 16:
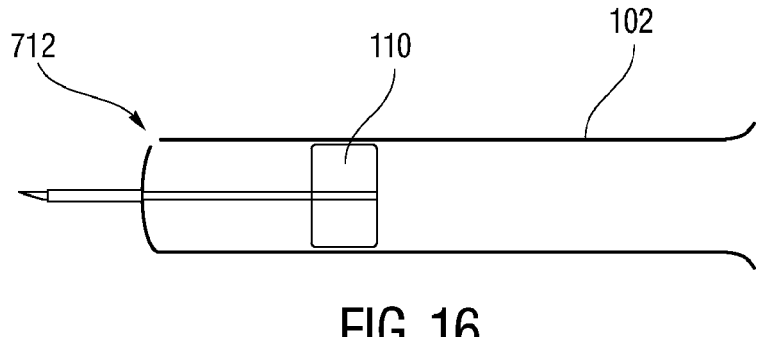
FIG. 16 shows an embodiment of an injection system of the present disclosure having an access port in the distal end.

In reference to FIG. 16, in some embodiments, the opening or the valve 712 in the distal region of the syringe may also be used to sterilize the section of the syringe between the floating sealing element and the distal end of the syringe. In particular, creating an access port in the portion of the syringe barrel, such as a valve or a hole, in front of the floating sealing element allows access for the sterilization gas or steam to easily enter that portion of the syringe. In some embodiments, such access port can be provided even if the lock is not used.

Figure 17A:
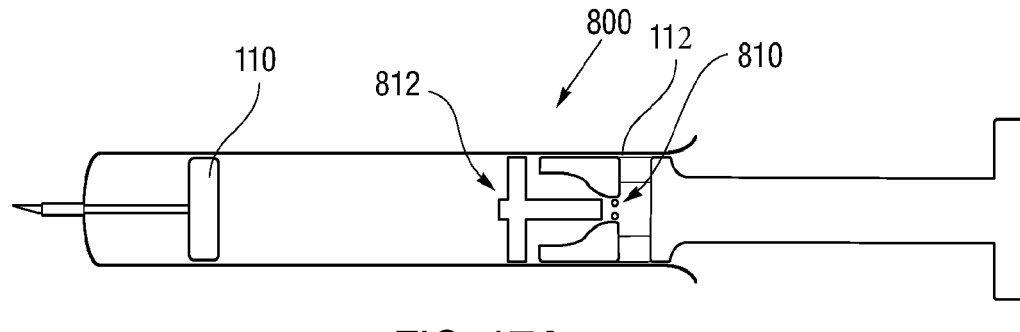
FIGS. 17A-17B show an embodiment of an injection system of the present disclosure having a touch trigger mechanism between the sealing elements.
Figure 17B:
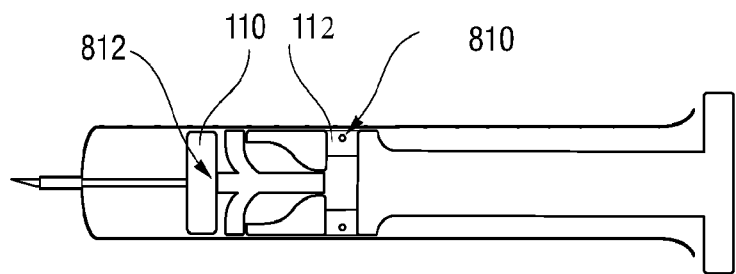

In reference to FIGS. 17A and 17B, in some embodiments, the safety feature to lock the floating sealing element comprises a touch trigger lock 800 disposed between the floating sealing element 110 and the pushing sealing element 112. Similar to the lock 700 discussed above, the touch trigger lock 800 can be configured to prevent the movement of the floating sealing element when the injection agent is delivered and, particularly, at the end of the delivery cycle when the pushing sealing element directly contacts the floating sealing element, which may bump the floating sealing element forward. In some embodiments, the touch trigger lock is a spring-loaded apparatus that springs outward into the inner portion of the syringe barrel when the pushing sealing element contacts the floating sealing element to increase friction between one or both sealing elements and the syringe barrel. In this manner, the touch trigger lock can serve as an anchor for the floating sealing element, the pushing sealing element or both to prevent their further movement once the touch trigger lock is discharged. In some embodiments, the touch trigger lock 800 comprises a resistance member 810 and a trigger 812 that releases the resistance member 810. The touch trigger mechanism can be disposed either on the floating sealing element or on the pushing sealing element, or on both. In operation, the resistance member is initially concealed in the touch trigger mechanism to enable the sealing elements to move freely within the syringe barrel. When the sealing elements come in contact with one another, the trigger 812 is activated to release the resistance member 810 from the touch trigger mechanism, which significantly increases the frictional forces between the syringe barrel and the sealing element with the touch trigger mechanism, thereby stopping that sealing element from advancing in the distal direction. Essentially, the resistance member acts as a brake to lock the sealing element in place. In some embodiments, the resistance mechanism can comprise a circular spring. In the initial configuration, the spring may be compressed within the touch trigger mechanism. When the trigger is activated, the circular spring is released from the touch trigger mechanism. The spring expands to make contact with the syringe barrel and to significantly increase friction between the one or both sealing element and the syringe barrel, which locks the one or both sealing elements in place.

In some embodiments, additionally or alternatively, a separate mechanical structure(s) can be provided that prevents advancement of the puncture element (e.g., another mechanical stop that prevents pushing sealing element from moving beyond a predetermined point). In operation, once the pushing sealing element is blocked from advancing, the floating sealing element cannot be pressurized and hence cannot be advanced further.

In some embodiments, the injection system of the present disclosure may be pre-filled with the injection agent during manufacturing, as described above. In some embodiments, the injection system of the present disclosure may be filled with the injection agent immediately prior to the administration of the injection agent to the patient. In some embodiments, the injection agent may be provided in a vial for storage and may be transferred to the SCS system by the user only when the injection agent is ready to be administered to the patient.

Figure 18:
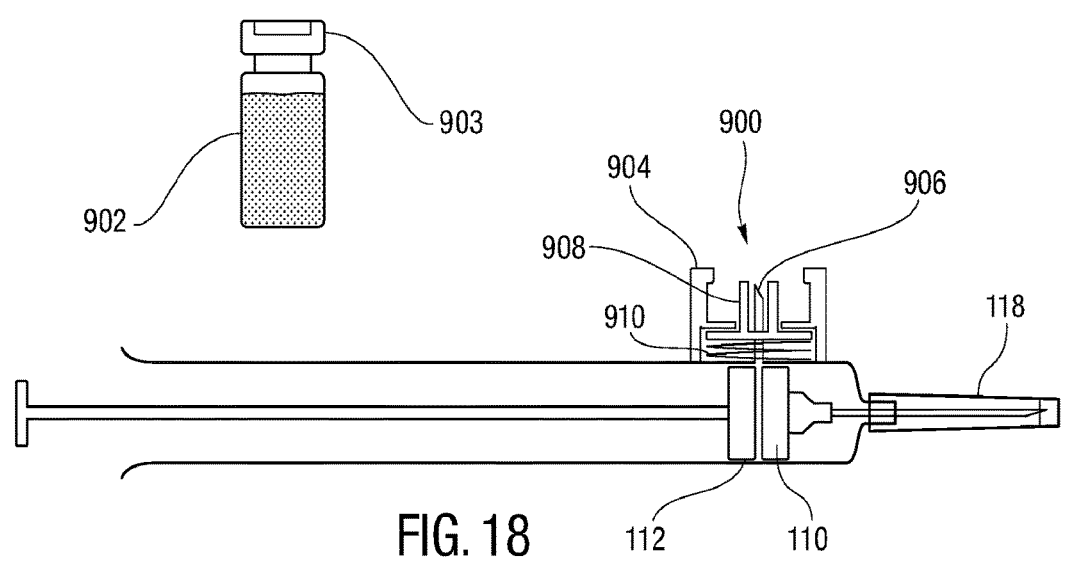
FIG. 18 shows an embodiment of an injection system of the present disclosure having a rapid fill port.

In reference to FIG. 18, in some embodiments, the injection system of the present disclosure is provided with a rapid fill port 900 to enable the loading of the injection agent into the injection chamber from a vial 902. In some embodiments, the rapid fill port 900 includes a receptacle 904 configured to accept the vial 902 to fluidly connect to vial to the injection chamber. In some embodiments, a hole or passageway is created (e.g. through molding, machining, etc.) through the wall of the syringe barrel proximal to the floating sealing element 110, and the receptacle 904 is placed over such hole or passageway. In some embodiments, when the floating sealing element is set in its initial position and the pushing sealing element is brought in contact with the floating sealing element, the rapid fill port is fluidly connected to the syringe barrel at the site between the sealing elements. Connected to the passageway, partially or fully disposed within it, is a side port fill needle 906 (preferably larger than the injection puncture element, such as an 18 gauge puncture element). Such fill needle can be beveled to pierce the elastomer cap 903 of the therapeutic containing vial 902. In some embodiments, the fill puncture element of the rapid fill port can have its opening on the side of the fill puncture element rather than at the tip. This side port can be covered by a casing or self-sealing puncture membrane 908 that blocks fluid flow when in the closed position. The casing 908 can be disposed within the receptacle and can be biased by a spring 910 to close the port of the fill needle when the vial is not present in its receptacle. In some embodiments, the safety cap 118 may be configured to provide an air tight seal when attached to the injection system.

Figure 19A:
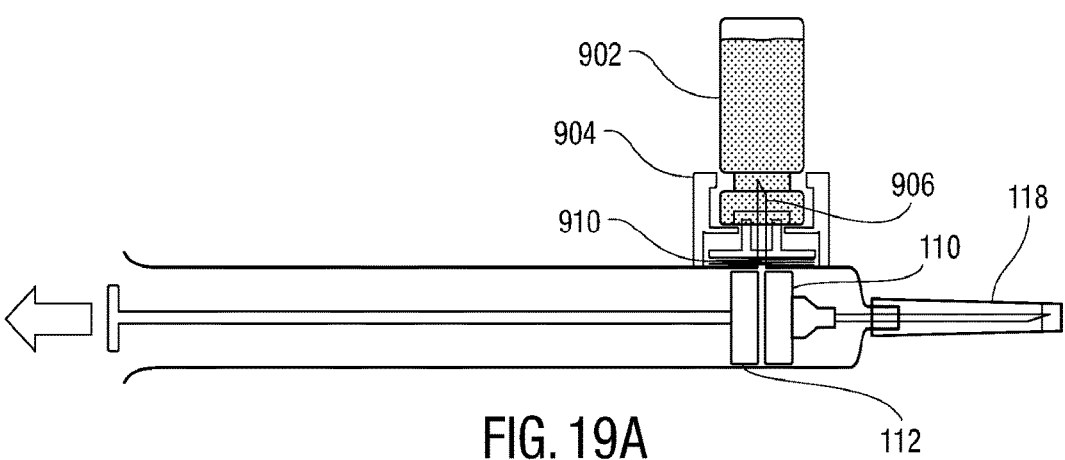
FIGS. 19A-19D illustrate an exemplary process of filling an injection system of the present disclosure through a rapid fill port.
Figure 19B:
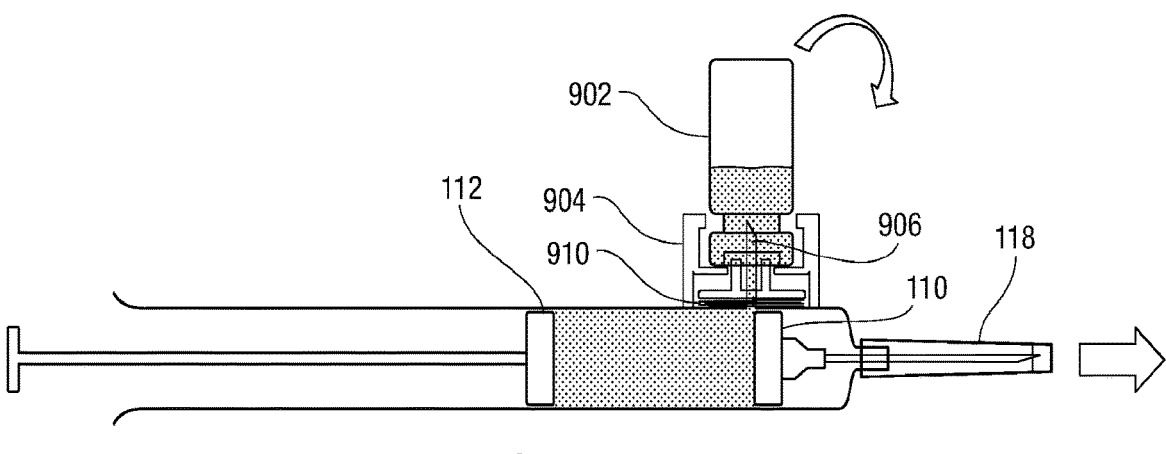

In operation, as shown in FIG. 19A, the vial 902 is snapped into the receptacle 904 of the rapid fill port 900, which forces the sliding fill puncture element casing away from the side port of the fill puncture element. The fill puncture element of the rapid fill port then penetrates through the stopper of the vial to fluidly connect the internal volume of the vial with the syringe barrel through the side port of the fill puncture element. In reference to FIG. 19B, the injection agent flows from the vial 902 into the injection chamber as the pushing sealing element 112 is withdrawn. In some embodiments, the safety cap is provided on the puncture element of the injection system to fluidically seal the puncture element so that when the pushing sealing element is withdrawn, bubbles are not drawn into the syringe barrel as well.

Figure 19C:
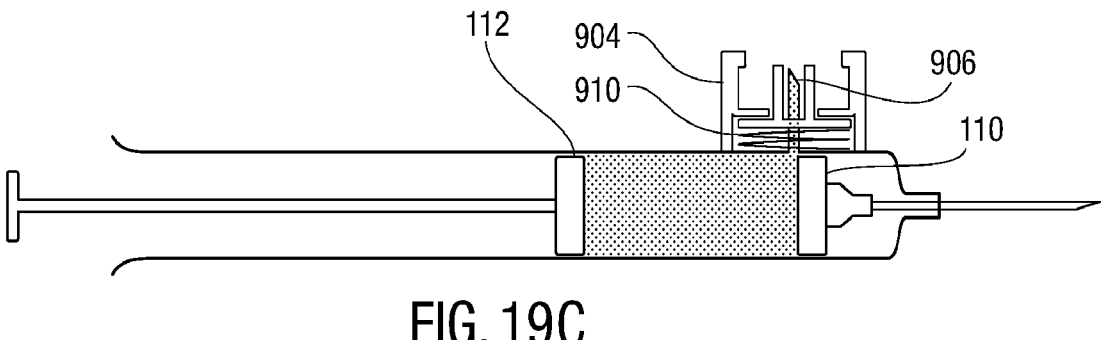
Figure 19D:
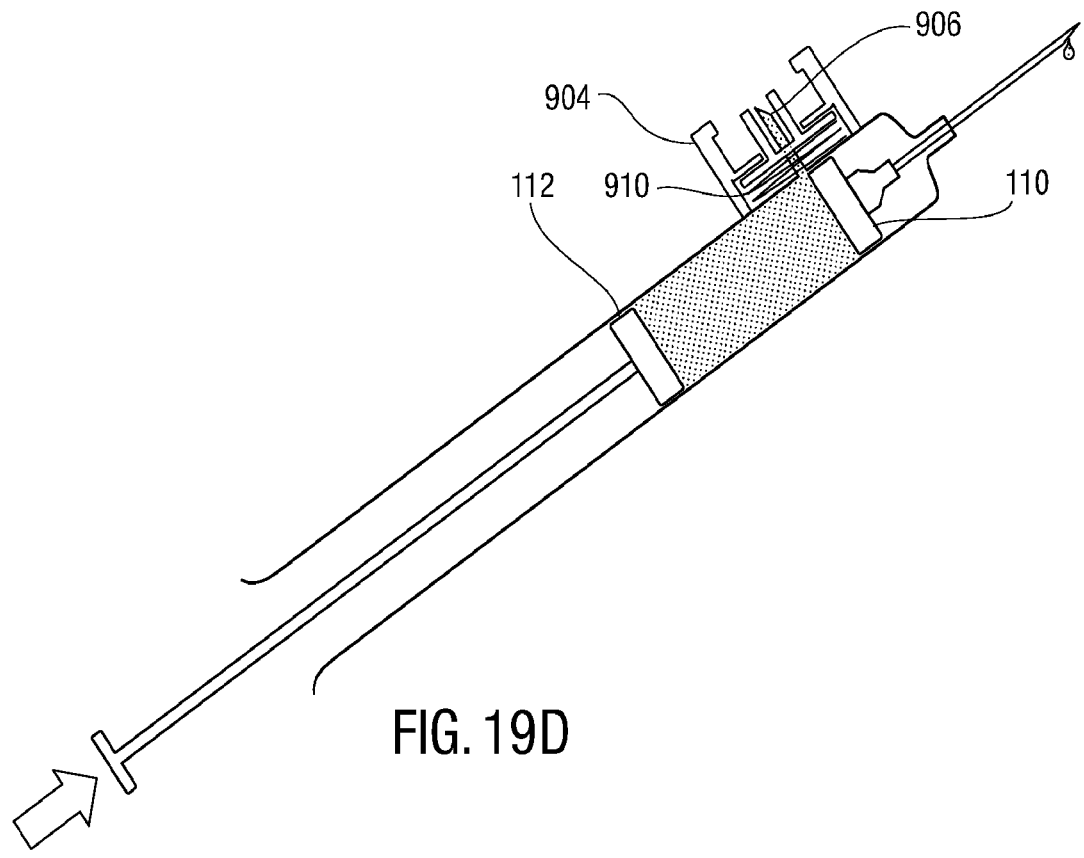

In reference to FIG. 19C, once the injection system is loaded with a desired amount of the injection agent, the vial can be removed from the receptacle of the rapid fill port, which allows the sliding fill puncture element casing to come up to seal the side port of the fill puncture element, which also seals the syringe barrel. The safety cap can be removed to allow fluid flow through the injection puncture element. As shown in FIG. 19D, the pushing sealing element can now be depressed until the injection fluid appears at the tip of the injection puncture element indicating that the injection puncture element has been cleared of air. In some embodiments, to assist in removing the air out of the puncture element, the injection system can be angled up. Then the injection system is ready for use. This rapid fill port design can enable filling the injection system with an injection agent at the point of care, while maintaining sterility outside of a sterile facility.

In some embodiments, the injection system of the present disclosure can be backfilled with the injection agent. This can take place during the initial manufacturing of the syringe or at a physician's office immediately prior to use.

Figures 20A, 20B, 20C, 21A, 21B:
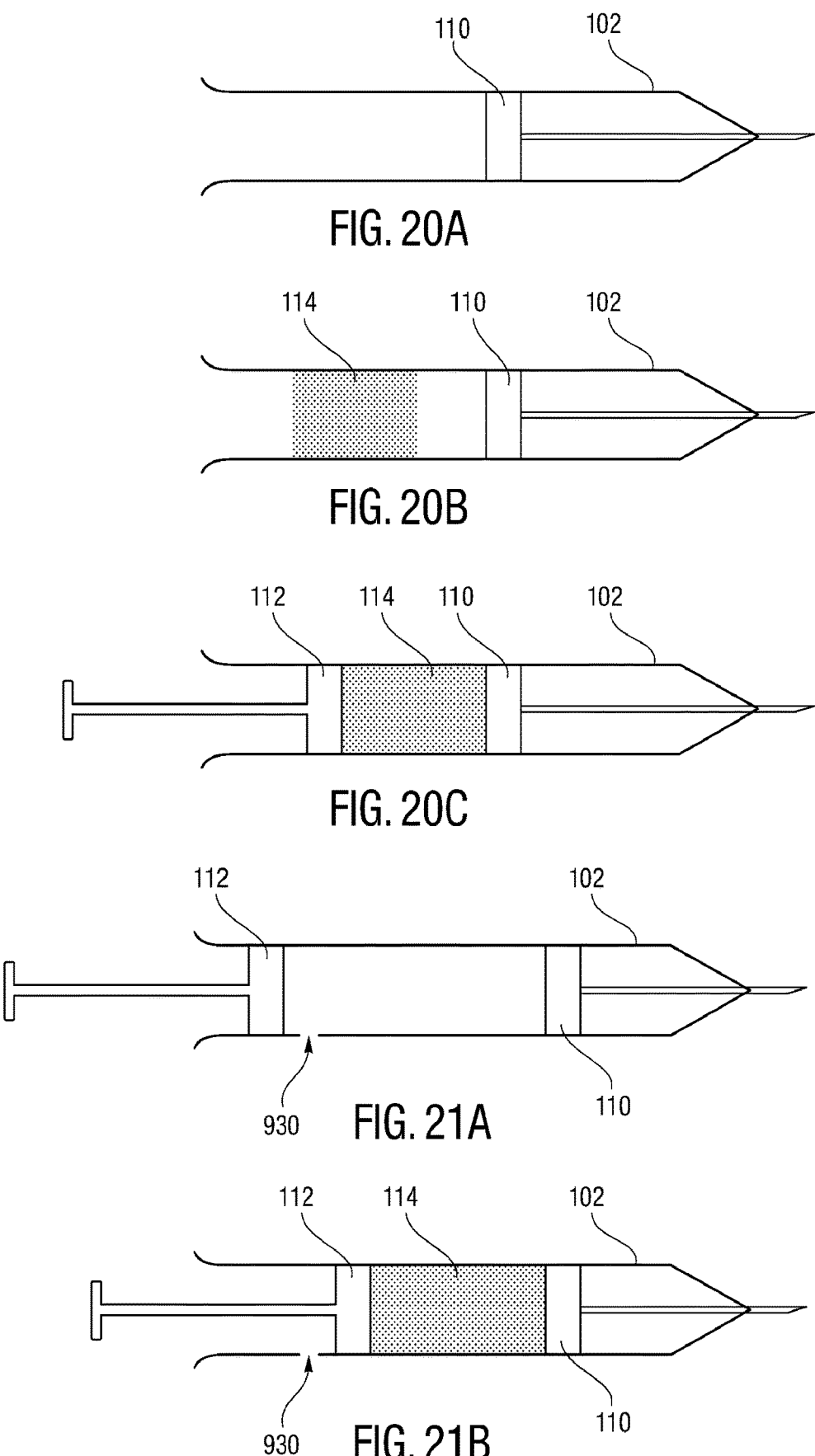
FIGS. 20A-20C show an exemplary process of back filling an injection system of the present disclosure.
FIGS. 21A-21B show an exemplary process of filling an injection system of the present disclosure through a port in the proximal end.

In some embodiments, as shown in FIG. 20A, the pushing sealing element can be removed, so the injection agent can be added to the syringe barrel through the back of the syringe barrel as shown in FIG. 20B. Next, as shown in FIG. 20C, the pushing sealing element can then be inserted and pushed toward the floating sealing element to remove any air in the injection puncture element and to prime the injection system for use.

In some embodiments, as shown in FIG. 21A, a fill port 930 may be provided in the proximal region of the syringe barrel 102 distal of the pushing sealing element 112. The injection agent 114 can be added to the injection system through this fill port 930 and then the pushing sealing element 112 can be pushed past the fill port 930, so that the pushing sealing element seals the injection fluid off from the fill port, as shown in FIG. 21B. In particular, the injection agent can be added to the injection system through the fill port using another sterile syringe/puncture element, while keeping puncture element side down (puncture element tip is blocked). In some embodiments, the total volume of the injection agent can be about 80% of the volume between the sealing elements. Then, the pushing sealing element can advance toward the floating sealing element to remove air through the fill port. After the pushing sealing element passes past the fill port, which blocks the fill port, the syringe can be flipped to bring the puncture element side up. Next, the pushing sealing element is advanced further in the distal direction to release the remaining air out of the syringe barrel and the injection puncture element.

Figure 22A:
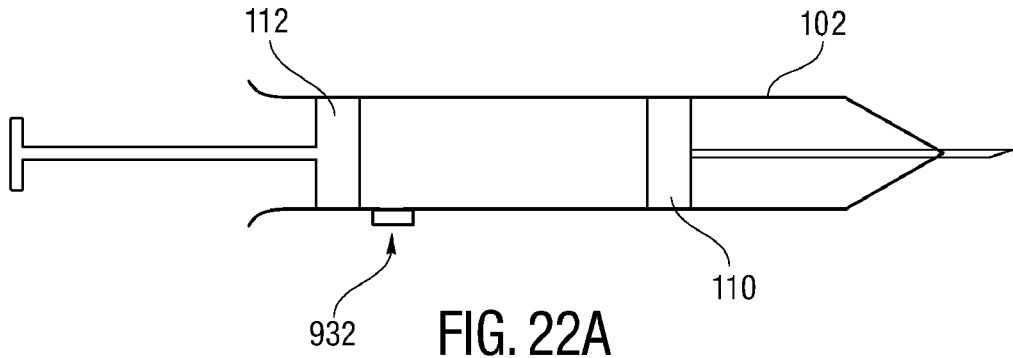
FIGS. 22A-22C show an exemplary process of filling an injection system of the present disclosure through a port sealed with a self-sealing polymer.
Figure 22B:
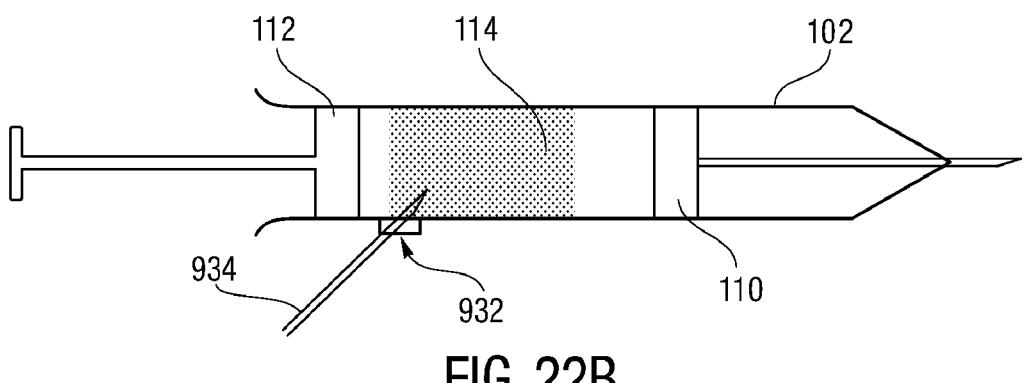
Figure 22C:
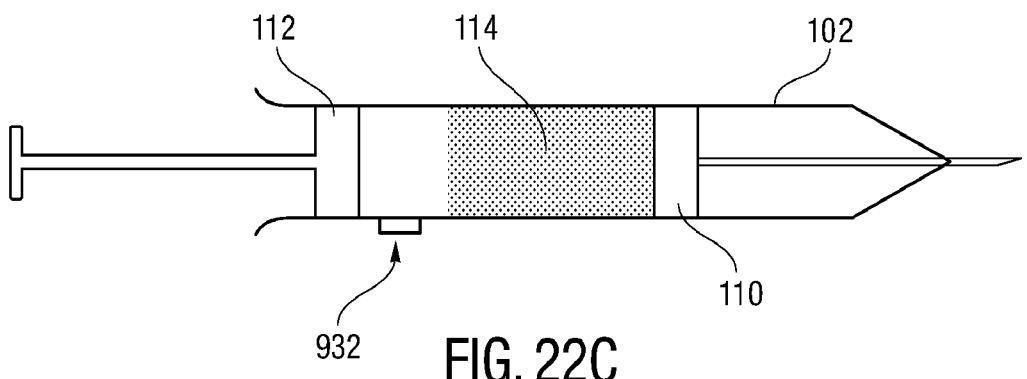
Figures 23A, 23B, 23C, 23D:
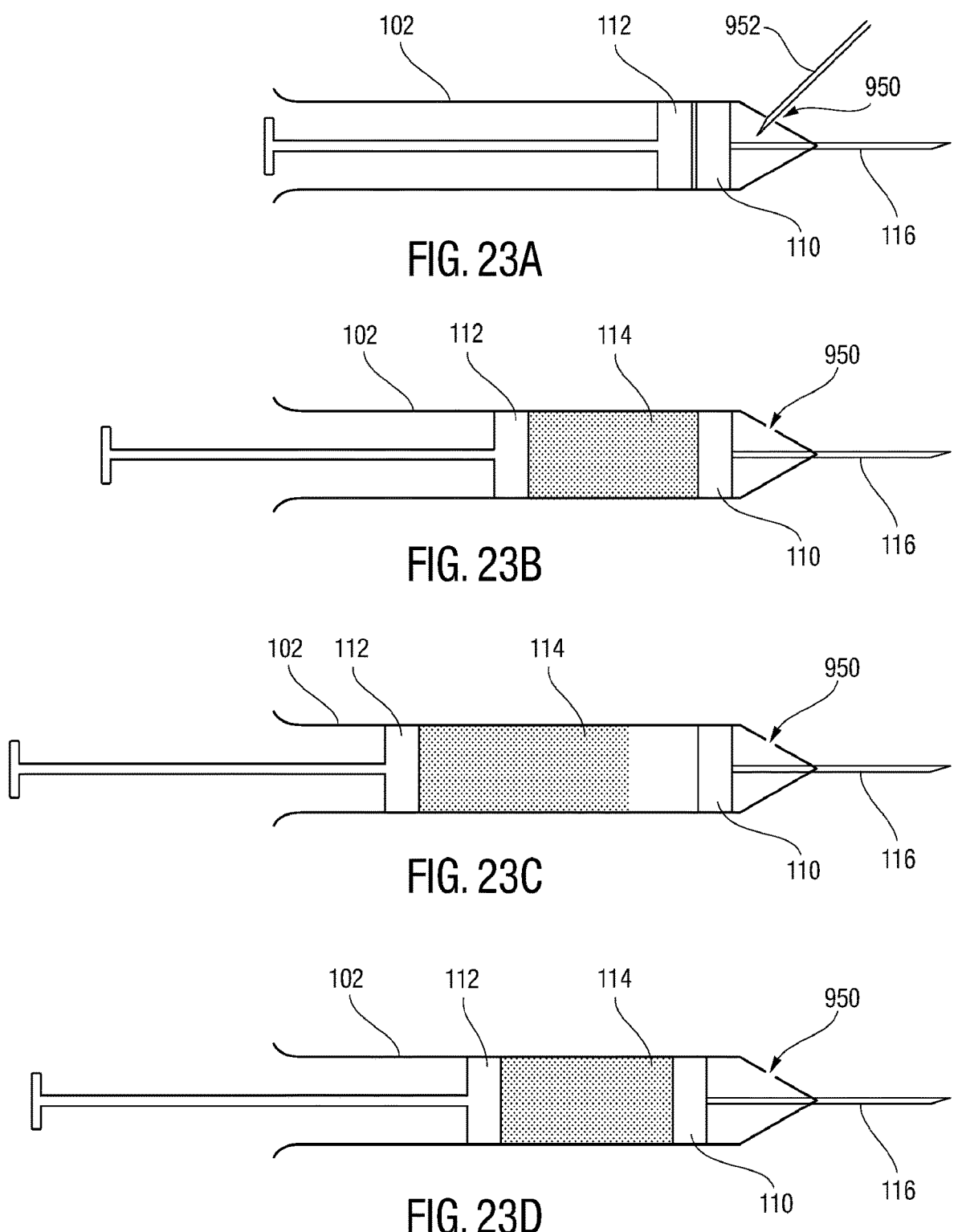
FIGS. 23A-23D show embodiments of an injection system of the present disclosure having a port in the distal end.

In some embodiments, as shown in FIG. 22A-22C, the fill port 930 (as shown in FIGS. 21A-21B) may be sealed using a self-sealing seal 932, (e.g. silicone rubber or polytetrafluoroethylene or a similar polymer). In this way, the fill port can be filled with a separate, larger bore loading needle 934 of a standard syringe, while the syringe barrel of the injection system can remain sealed throughout the process. When the loading puncture element is removed from the fill port, the fill port self-seals sufficiently to not leak under pressure applied by the pushing sealing element during use.

In some embodiments, as shown in FIG. 23A-23D, a fill port 950 may be provided in the distal portion of the syringe barrel 102 distally of the floating sealing element 110. This can enable the user to access the floating sealing element with a pushing tool 952 (e.g. a long, thin, rigid object that fits in the hole and is long enough to reach the outside) to set the floating sealing element in a desired position from the distal end of the syringe barrel. For example, when using the rapid fill port 900, the injection element can be extended outwards so that it can be pushed through an elastomeric vial stopper, then the injection agent can be drawn into the syringe by withdrawing the pushing sealing element. The pushing sealing element can then be withdrawn further in the proximal direction, so that the floating sealing element can be pushed back to its pre-insertion position within the syringe barrel.

In some embodiments, the volume of the injection chamber is between 20 and 200 microliters. For improved haptics, in some embodiments, the stroke length of the pushing sealing element to deliver the therapeutic fluid or suspension is at least 1 centimeter in length. For some embodiments, the flow rate of injection is targeted to be between 0.2 and 20 microliters per second on average. In some embodiments, the syringe barrel is lined in silicone rubber, glass, polytetrafluoroethylene, or polypropylene to minimize adsorption of the therapeutic to the syringe barrel inner surface.

Figure 24A:
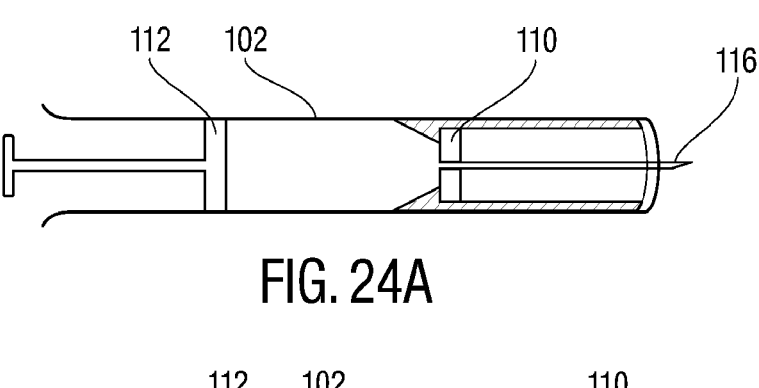
FIGS. 24A-24E show an embodiment of an injection system of the present disclosure configured for safe disposal.
Figure 24B:
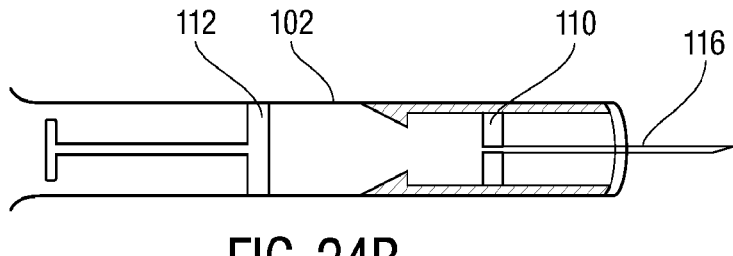
Figure 24C:
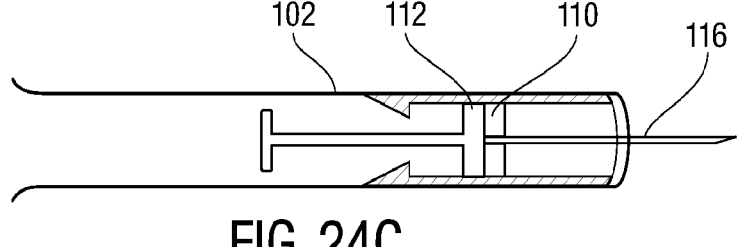
Figure 24D:
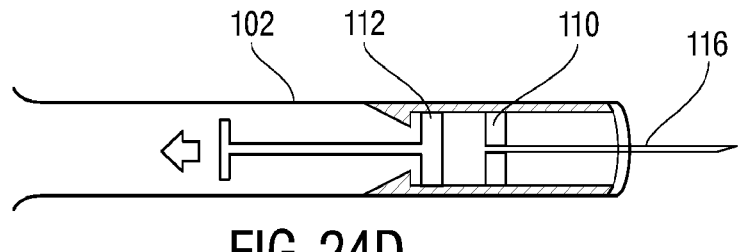
Figure 24E:
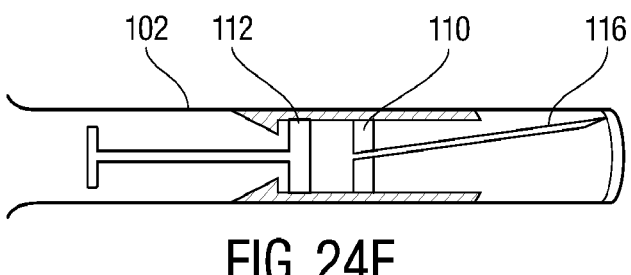

In some embodiments, in reference to FIGS. 24A-24E, the injection system of the present disclosure is configured for safe disposal. In some embodiments, at the end of the injection cycle, as shown in FIGS. 24A and 24B, the pushing sealing element 112 may come in contact with the floating sealing element 110, as shown in FIG. 24C. In some embodiments, the injection system is configured such that the pushing plunger may then couple, directly or indirectly as shown in FIG. 24D, to the floating sealing element. Once the sealing elements are coupled, the pushing sealing element may be withdrawn, thereby causing the floating sealing element and the puncture element to also be withdrawn into the syringe barrel, as shown in FIG. 24D. In some embodiments, the puncture element is configured so it can be deflected within the syringe barrel, so it can no longer be extended outside the syringe barrel as shown in FIG. 24E.

In some embodiments, the injection system of the present disclosure is used to deliver a viral gene delivery vector or vectors, including, but not limited to adeno-associated virus (AAV), a variant or serotype thereof, including but not limited to AAV serotypes 1-11, particularly AAV1, AAV2, AAV3, AAV4, AAV5, AAV6, AAV7, AAV8, AAV9, AAV10 and AAV11, and recombinant serotypes such as Rec2 and Rec3 to treat a genetic disorder of disease of the retina or choroid. AAV1, AAV2, AAV4, AAV5, AAV6, AAV7, AAV8, and AAV9 can all display tropism for retinal tissue, including retinal pigment epithelium and photoreceptors, as described in https://www.retinalphysician.com/issues/2020/special-edition-2020/vector-considerations-for-ocular-gene-therapy, incorporated herein by reference in its entirety. Exemplary diseases can include, but not limited to wet age-related macular degeneration, dry age-related macular degeneration (AMD), glaucoma, choroideremia, and other heritable vision diseases and disorders. In some embodiments, the injection system is used to deliver a viral delivery vector or vectors, including, but not limited to AAV, or a variant thereof, to transfect retinal and/or choroidal cells, such as including, but not limited to, photoreceptors, pigmented cells, bipolar cells, ganglion cells, horizontal cells, and amacrine cells, vascular endothelial cells, vascular smooth muscle cells, non-vascular smooth muscle cells, melanocytes, fibroblasts, resident immunocompetent cells, with anti-vascular endothelial growth factor (anti-VEGF), and anti-vascular endothelial growth factor receptor (anti-VEGFR) gene that when transcribed produces an anti-VEGF protein or proteins for treating wet AMD. In some embodiments, the gene therapy compositions may also include a promoter for the gene of interest.

In some embodiments, the injection system is used to deliver gene therapies including, but not limited to small interfering ribonucleic acids (siRNAs), short hairpin ribonucleic acids (shRNAs), micro-ribonucleic acids (microRNAs), closed end-deoxyribonucleic acids (ceDNAs), polymer-DNA conjugates, or clustered regularly interspaced short palindromic repeats (CRISPR) and CRISPR-associated protein 9 (Cas9) systems, and variants thereof, and transcription activator-like effector nucleases (TALENs) and variants thereof, and zinc finger nucleases (ZFNs) and variants thereof and transposon-based gene delivery such as the Sleeping Beauty (SB), piggyBac (PB), Tol2 or variants thereof. These gene therapies can be packaged in viral vectors, non-viral vectors or nanoparticles.

In some embodiments, the injection system is used to deliver a viral gene delivery vector or vectors, non-viral gene delivery systems or other gene therapies achieves a transfection efficiency of the retinal and/or choroidal cells of less than 0.001%, 0.01%, 0.1%, 1%, 3%, 5%, 10%, 25%, 50%, 75% or 90%.

In some embodiments, the injection system is used to deliver a small or large molecule therapy targeted against VEGF or VEGFR, such as including, but not limited to, ziv-aflibercept, pazopanib, bevacizumab, cabozantinib, sunitinib, sorafenib, axitinib, regorafenib, ponatinib, cabozantinib, vandetanib, ramucirumab, lenvatinib, and bevacizumab.

In some embodiments, the injection system is used to deliver a gene therapy that targets, replaces, inhibits, or promotes one or more of the following genes to impart a therapeutic effect for a hereditary ocular disease or disorder including, but not limited to, MTP, HGD, SLC16A2, POLG, ALMS1, FGFR2, PRPS1, APTX, ATM, DNMT1, TGFBI, ACTB, FGFR2, BEST1, CYP4V2, NOD2, FOXL2, ABCC9, ERCC6, CYP27A1, CHS1, SH3BP2, HDAC6, CHM, SLC9A6, NSDHL, OPN1MW, OPN1LW, OPN1SW, KERA, IGBP1, OPA3, UGT1A1, FGFR2, FGFR3, ATP6V0A2, CTNS, EFEMP1, SALL4, ADAMTSL4, FBN1, ADAMTSL4, NR2E3, TGFBI, GLA, IKBKAP, LCAT, GALK1, GALT, GBA, GLB1, PORCN, TGFBI, OAT, ENG, CBS, MBTPS2, IKBKG, CNNM4, ATRX, GALC, TGFBI, HADHA, OCRL1, PLP1, B3GALTL, PAH, ARX, LOXL1, TGFBI, PQBP1, RB1, IDUA, IDS, SGSH, NAGLU, HGSNAT, GNS, GALNS, GLB1, ARSB, GUSB, FGFR3, LMX1B, NHS, STAC3, NF1, NF2, NF1, MT-ATP6, NDP, RP1L1, GPR143, PABN1, HEXB, UBIAD1, AGK, RAIL, HBB, TIMP3, ATP2B3, ABCA4, ELOVL4, PROM1, GNAQ, SUOX, NAA10, BCOR, SOX2, OTX2, BMP4, HCCS, STRA6, VAX1, RARB, HMGB3, MAB21L2, RBM10, HEXA, TGFBI, SHOX, TAT, PTEN, VHL, VCAN, NF1, ZC4H2, ATP7B, CNGA3, CNGB3, JAG1, NOTCH2, PAX6, ELP4, FOXES, PITX3, PITX2, FOXC1, CHD7, SEMA3E, ERCC6, ERCC8, CYP1B1, MYOC, MYOC, CYP1B1, FGFR1, FGFR2, FGFR1, FGFR2, NDN, SNRPN, PHYH, PEX7, CREBBP, EP300, OPA1, OPTN, SAG, GRK1, TWIST1, FGFR2, GPC3, OFD1, TSC1, TSC2, PRPH2, BEST1, WFS1, CISD2, COL4A5, COL4A4, COL4A3, UBE3A, CDKLS, MECP2, PTCH1, PTCH2, SUFU, NSD1, H19, KCNQ1OT1, CDKN1C, OPN1LW, OPN1MW, EYA1, SIX1, SIX5, KIF21A, PHOX2A, ARIX, TUBB3, SMC1A, HDAC8, COL5A1, COL5A2, COL3A1, TNXB, OPTN, ASB10, WDR36, MTND1, MTND4, MTNDS, MTND6, PAX6, PITX2, CYP1B1, FOXCl, DMPK, ZNF9, CNBP, NPC1,

27

NPC2, SMPD1, TYR, OCA2, TYRP1, or SLC45A2, MC1R, COL1A1, COL1A2, CRTAP, LEPRE1, NPHP1, NPHP4 SDCCAG8, WDR19, CEP290, IQCB1, HESX1, OTX2, SOX2, COL2A1, COL11A1, COL11A2, COL9A1, COL9A2, MYO7A, USH2A, EDN3, EDNRB, MITF, PAX3, SNAI2, SOX10, ADAMTS10, FBN1, LTBP2, XPA, XPC, ERCC2, ERCC3, and POLH.

In some embodiments, the delivery system of the present disclosure may be used to deliver gene therapy to treat age-related macular degeneration (AMD) or diabetic macular edema (DME). In some embodiments, the delivery system of the present disclosure is used for suprachoroidal (SCS) delivery of a composition comprising a AAV vector including one or more genes to block VEGFR-2, optionally with a CAG promoter. In some embodiments, other suitable promoters include, but are not limited to, human bestrophin (hVMD2), cytomegalovirus (CMV), SV40, mGluR6, CB7, UbiC, RZ, RedO, Rho and Best1. In some embodiments, such system may include a 25-34 gauge puncture element with a polypropylene or glass syringe and fluoropolymer, silicone or rubber for the pushing sealing element stopper and floating sealing element stopper. In some embodiments, about 80-120 (for example, 100) microliters of such gene therapy composition can be delivered over 5-60 seconds. In some embodiments, the puncture element may have a bevel length less than 2 mm, less than 1 mm or less than 0.5 mm. The bevel angle can be greater than 15 degrees, greater than 30 degrees, or even greater than 45 degrees. In some embodiments, the puncture element can be 25 gauge and higher, 27 gauge and higher, or 30 gauge or higher. In some embodiments the needle has a secondary bevel to lower cutting forces.

In some embodiments, the delivery system is utilized to deliver small or large molecule injection agents such as, anti-VEGF drugs including, but not limited to, bevacizumab, ranibizumab, aflibercept, Ramucirumab, disintegrins, anti-prostaglandins, tryptophanyl-tRNAsynthetase-derived polypeptides, Inosine monophosphate dehydrogenase (IMPDH) inhibitors and anti-PDGF to treat AMD; and corticosteroids to treat uveitis, chorioretinitis, or other inflammatory eye diseases; botulinum toxin for various ocular applications; tyrosine kinase inhibitors (such as Vandetanib, Axitinib, Pazopanib, Sunitinib, Sorafenib) to treat pterygium, dry eye or AMD; levo-betaxolol, or other betaadrenoceptor antagonists and 5-HT1A agonists to treat retinal pathologies.

In some embodiments, the injection system is used to deliver small molecule Wnt inhibitors to decrease angiogenesis. These small molecular Wnt inhibitors can include indazole-3-carboxamide compound or analogs thereof (WO2013040215A1), y-diketones or salts or analogs thereof (WO2014130869A1), azaindazole compound or analogs (e.g. 3-(1h-benzo[d]imidazol-2-yl)-1h-pyrazolo[3,4-c]pyridine) thereof (WO2016040180A1), N-(5-(3-(7-(3-fluorophenyl)-3H-imidazo[4,5-c]pyridin-2-yl)-1H-indazol-5-yl)pyridin-3-yl)-3-methylbutanamide, including amorphous and polymorph forms thereof (WO2017210407A1), Isoquinolin-3-yl carboxamides or salt or analogs and including amorphous and polymorph forms thereof (WO2017189823A2), Diazanaphthalen-3-yl carboxamides or salt or analogs and including amorphous and polymorph forms (US20190127370A1), 6-(5-membered heteroaryl)isoquinolin-3-yl-(5-membered heteroaryl) carboxamides or salt or analogs and including amorphous and polymorph forms (WO2019084496A1), 6-(6-membered heteroaryl & aryl)isoquinolin-3-yl carboxamides or salt or analogs and including amorphous and polymorph forms (US20190125740A1), 3-(3h-imidazo[4,5-b]pyridin-2-yl)-1h-pyrazolo[3,4-b]pyridine (US20190119303A1), Wnt inhibitors containing an indazole core or salt or analogs and including amorphous and polymorph forms (WO2013151708A1), 1h-pyrazolo[3, 4-b]pyridines or salt or analogs and including amorphous and polymorph forms (WO2013166396A2), 2-(1h-indazol-3-yl)-3h-imidazo[4,5-b]pyridine or salt or analogs and including amorphous and polymorph forms (US20190055238A1), f3-diketone, y-diketone or y-hydroxyketone or salts or analogs thereof (WO2012024404A1), 3-(benzoimidazol-2-yl)-indazole inhibitors or salt or analogs and including amorphous and polymorph forms (US10183929B2), 3-(1h-imidazo[4,5-c]pyridin-2-yl)-1h-pyrazolo[3,4-b]pyridine or salt or analogs and including amorphous and polymorph forms (US20180325910A1), 1H-pyrazolo [3,4-b] pyridines or salt or analogs and including amorphous and polymorph forms (CY-1119844-T1), 3-(1h-imidazo[4,5-c]pyridin-2-yl)-1h-pyrazolo[3,4-c]pyridine or salt or analogs and including amorphous and polymorph forms (US-2018250269-A1), N-(5-(3-(7-(3-fluorophenyl)-3H-imidazo[4,5-c]pyridin-2-yl)-1H-indazol-5-yl)pyridin-3-yl)-3-methylbutanamide or salt or analogs and including amorphous and polymorph forms, (US20180133199A1), indazole-3-carboxamides or salt or analogs and including amorphous and polymorph forms (US-2018185343-A1), 3-(3h-imidazo[4,5-b]pyridin-2-yl)-1h-pyrazolo[3,4-c]pyridine or salt or analogs and including amorphous and polymorph forms (US-2018201624-A1), 2-(1h-indazol-3-yl)-1h-imidazo[4,5-c]pyridine or salt or analogs and including amorphous and polymorph forms (US-2018215753-A1), 3-(3H-imidazo[4,5-C]pyridin-2-yl)-1H-pyrazolo[3,4-C]pyridine or salt or analogs and including amorphous and polymorph forms (US-10052331-B2), 5-substituted indazole-3-carboxamides or salt or analogs and including amorphous and polymorph forms (US-2018127377-A1), 3-(3H-imidazo[4,5-C]pyridin-2-yl)-1H-pyrazolo[4,3-B]pyridines or salt or analogs and including amorphous and polymorph forms (US-10188634-B2), 3-(1H-imidazo[4,5-C]pyridin-2-yl)-1H-pyrazolo[4,3-B]pyridines or salt or analogs and including amorphous and polymorph forms (US-10195185-B2), 3-(1h-pyrrolo[2,3-b]pyridin-2-yl)-1h-indazoles or salt or analogs and including amorphous and polymorph forms (W0-2017024021-A1), 3-(1h-pyrrolo[2,3-c]pyridin-2-yl)-1h-pyrazolo[3,4-c]pyridines or salt or analogs and including amorphous and polymorph forms (W0-2017023975-A1), 3-(1h-indol-2-yl)-1h-pyrazolo[3,4-b]pyridines or salt or analogs and including amorphous and polymorph forms (US-2018214428-A1), 3-(1h-pyrrolo[3,2-c]pyridin-2-yl)-1h-indazoles or salt or analogs and including amorphous and polymorph forms (US-2018221350-A1), 3-(1h-indol-2-yl)-1h-indazoles or salt or analogs and including amorphous and polymorph forms (W0-2017023986-A1), 3-(1H-pyrrolo[2,3-B]pyridin-2-yl)-1H-pyrazolo[4,3-B]pyridines or salt or analogs and including amorphous and polymorph forms (US-10206909-B2), 3-(1h-pyrrolo [3,2-c]pyridin-2-yl)-1h-pyrazolo [4,3-b] pyridines or salt or analogs and including amorphous and polymorph forms (WO-2017024003-A1), 3-(1h-pyrrolo[3,2-c]pyridin-2-yl)-1h-pyrazolo[3,4-b]pyridines or salt or analogs and including amorphous and polymorph forms (US-2018221341-A1), 3-(3h-imidazo[4,5-b]pyridin-2-yl)-1h-pyrazolo[4,3-b]pyridines or salt or analogs and including amorphous and polymorph forms (W0-2017024015-A1), 3-(1h-pyrrolo[2,3-c]pyridin-2-yl)-1h-pyrazolo[3,4-b]pyridines or salt or analogs and including amorphous and polymorph forms (US-2018221352-A1), 3-(1H-pyrrolo[3,2-C]pyridin-2-YL)-1H-pyrazolo[3,4-C]pyridines or salt or analogs and including amorphous and polymorph forms (US-10206908-B2). Each of the references referenced herein are incorporated by reference in their entirety.

In some embodiments, the injection system is utilized to deliver suspensions of injection agents including microencapsulated agents, nanoencapsulated agents, pure protein nanoparticles and poorly water-soluble or water-insoluble agents.

In some embodiments, the injection agent or encapsulated injection agent is delivered with a residence time extending matrix. The matrix can consist of reverse thermally responsive hydrogels, self-assembling hydrogels, bioadhesive polymer networks, hydrogels, fibronectin-containing hydrogels, enzyme-responsive hydrogels, ultrasound sensitive hydrogels, pH-sensitive hydrogels, carbohydrates, two or more component hydrogels, and multi-component double network hydrogels.

In some embodiments, the injection agent is delivered via the injection system with following a permeation enhancer such as including, but not limited to, dimethylsulfoxide (DMSO), collagenases, elastases, proteases, papain, bromelain, peptidases, lipases, alcohols, polyols, short chain glycerides, amines, amides, cyclodextrins, fatty acids, pyrrolidones, Cyclopentadecalactone, Sodium N-[8-(2-hydroxylbenzoyl)amino] caprylate (SNAC), 8-(N-2-hydroxy-5-chloro-benzoyl)-amino-caprylic acid (5-CNAC), Sodium caprate, Sodium caprylate, omega 3 fatty acid, protease inhibitors, alkylglycosides, chitosan, Dodecyl-2-N, N-dimethylamino propionate (DDAIP), N-methyl-2-pyrrolidone (NMP), azones, sulfoxides, surfactants, benzylalkonium chloride, saponin, bile salts, bile acids, cell penetrating peptides, polyarginine, low molecular weight protamine, polyserine, capric acid, gelucires, semifluorinated alkanes, terpenes, phospholipids, chelators, Ethylenediamine Tetraacetic acid (EDTA), citrate, crown ethers and combinations thereof.

In some embodiments, the injection agent having one or more therapeutic formulations is delivered via the injection system with or following administration of one or more vasoconstrictive agents to reduce efflux of the injection agent via the choroidal blood vessels, including, but not limited to 25I-NBOMe, Amphetamines, AMT, Antihistamines, Caffeine, Cocaine, Dopamine, Dobutamine, DOM, LSA, LSD, Methylphenidate, Mephedrone, Norepinephrine, Oxymetazoline, Phenylephrine, Propylhexedrine, Pseudoephedrine, Stimulants, Serotonin 5-hydroxytryptamine agonists, triptans and Tetrahydrozoline hydrochloride. In some embodiments, these agents may be administered using the injection system of the present disclosure into the SCS or via an intravitreal injection using a standard syringe. The vasoconstrictive agents can be delivered before, simultaneously, or after the administration of the one or more therapeutic formulations.

In some embodiments, the injection agent delivered via the injection system achieves SCS coverage in excess of 20%, 40%, 60% or 80%.

In some embodiments, the injection agent delivered via the injection system with or without one or more vasoconstrictive agents to reduce efflux of the injection agent via the choroidal blood vessels achieves SCS coverage in less than 180, 120, 60, 30 or 15 minutes.

In some embodiments, the injection agent delivered via the injection system has a retention time within the SCS of less than 180, 120, 60, 30, 15, 10 or 5 minutes.

In some embodiments, the injection agent is delivered via the injection system in less than 500, 400, 300, 200 or 100 microliters.

In some embodiments, the injection agent is delivered via the injection system in concentrations less than 80%, 60%, 40% 20%, 10%, 5%, 2.5% or 1%.

In some embodiments, the percent dosage of the injection agent delivered via the injection system delivered to the subretinal space is less than 80%, 60%, 40% 20%, 10%, 5%, 2.5% or 1%.

In some embodiments, the injection agent delivered via the injection system is dosed at least once every 10 years, once every 5 years, once every 2 years, once every 1 year, once every 6 months, once every 3 months, once a month or once a week.

In some embodiments, the injection system is used to deliver one or multiple injection agents to treat one or more of the ocular causes or effects of the following diseases including, but not limited to, Abetalipoproteinemia (Bassen-Kornzweig Syndrome), Alkaptonuria, Allan-Herndon-Dudley Syndrome, Alpers Syndrome, Alstrom Syndrome, Apert Syndrome, Arts Syndrome (Mental Retardation, X-Linked, Syndromic 18), Ataxia-Oculomotor Apraxia Syndrome, Ataxia Telangiectasia (Louis-Bar Syndrome), Autosomal Dominant Cerebellar Ataxia Deafness and Narcolepsy (AD-CADN), Avellino Corneal Dystrophy (Combined Granular-Lattice Corneal Dystrophy), Baraitser-Winter Syndrome 1, Beare-Stevenson Syndrome, Best Macular Dystrophy, Bietti Crystalline Comeoretinal Dystrophy, Blau Syndrome, Blepharophimosis, Ptosis, and Epicanthus Inversus (BPES), Cantu Syndrome, Cerebrooculofacioskeletal Syndrome, Cerebrotendinous Xanthomatosis, Chediak-Higashi Syndrome, Cherubism, Chondrodysplasia with Platyspondyly, Distinctive Brachydactyly, Hydrocephaly, and Microphthalmia, Choroideremia, Christianson Syndrome, CK Syndrome, Colorblindness, Deutan, Colorblindness, Protan, Colorblindness, Tritanopic, Cornea Plana, Corpus Callosum, Agenesis of, with Mental Retardation, Ocular Coloboma, and Micrognathia, Costeff Syndrome, Crigler-Najjar, Crouzon Syndrome, Crouzon Syndrome with Acanthosis Nigricans (Crouzonodermoskeletal Syndrome), Cutis Laxa, Debre Type, Cystinosis, Doyne Honeycomb Dystrophy (Malattia Leventinese), Duane-Radial Ray Syndrome, Ectopia Lentis et Pupillae, Ectopia Lentis, Familial, Ectopia Lentis, Isolated, Enhanced S-Cone Syndrome, Epithelia Basement Membrane Corneal, Dystrophy (Map-Dot-Fingerprint Corneal Dystrophy), Fabry Disease (Hereditary, Dystopic Lipidosis), Familial Dysautonomia, Fish-Eye Disease, Galactokinase Deficiency, Galactosemia, Gaucher's Disease, GM1-Gangliosidosis, Type I, GM1-Gangliosidosis, Type II, GM1-Gangliosidosis, Type III, Goltz Syndrome, Granular, Corneal Dystrophy (Groenouw Type I), Gyrate Atrophy, Hereditary Hemorrhagic Telangietasia (Osler-Rendu-Weber Disease), Homocystinuria, IFAP Syndrome with or without Bresheck Syndrome, Incontinentia Pigmenti (Bloch-Sulzberger Syndrome), Jalili Syndrome, Juberg-Marsidi Syndrome, Krabbe Disease, Lattice Corneal Dystrophy, LCHAD (Long-Chain 3-Hydroxyacyl-Coa Dehydrogenase) Deficiency, Lowe, Pelizaeus-Merzbacher, Peters-Plus Syndrome (Krause-Kivlin Syndrome), Phenylketonuria, Proud Syndrome, Pseudoexfoliation Syndrome, Reis-Bucklers Corneal Dystrophy, Renpenning Syndrome (Mental Retardation, X-Linked, Renpenning Type), Retinoblastoma, Retinoschisis, Juvenile X Linked, Russell-Silver Syndrome, Mucopolysaccharidosis Type IH (Hurler Syndrome), Mucopolysaccharidosis Type IH/S (Hurler-Scheie Syndrome), Mucopolysaccharidosis Type IS (Scheie Syndrome), Mucopolysaccharidosis Type II (Hunter Syndrome), Mucopolysaccharidosis Type IIIA (Sanfilippo Syndrome A), Mucopolysaccharidosis Type IIIB (Sanfilippo Syndrome B), Mucopolysaccharidosis Type IIIC (Sanfilippo Syndrome C), Mucopolysaccharidosis Type IIID (Sanfilippo Syndrome D), Mucopolysaccharidosis Type IVA (Morquio Syndrome A), Mucopolysaccharidosis Type IVB (Morquio Syndrome B), Mucopolysaccharidosis Type VI (Maroteaux-Lamy Syndrome), Mucopolysaccharidosis Type VII (Sly Syndrome), Muenke Syndrome, Nail-Patella Syndrome, Nance-Horan Syndrome Native American Myopathy, Neurofibromatosis Type I, Neurofibromatosis Type II, Neurofibromatosis-Noonan Syndrome, Neuropathy, Ataxia, and Retinitis, Pigmentosa (NARP), Norrie Disease, Occult Macular Dystophy, Ocular Albinism, Oculopharyngeal Muscular Dystrophy, Sandhoff Disease (GM2-Gangliosidosis, Type II), Schnyder Corneal Dysrophy, Sengers Syndrome, Smith-Magenis Syndrome, (Chromosome 17p11.2 Deletion Syndrome), Sickle Cell Anemia, Sorsby Fundus Dystrophy, Spinocerebellar Ataxia, X-Linked 1, Stargardt Disease/Fundus, Flavimaculatus, Sturge-Weber Syndrome, Sulfocysteinuria (Sulfite Oxidase Deficiency), Syndromic Microphthalmia 1 (Lenz Microphthalmia Syndrome), Syndromic Microphthalmia 2 (Oculofaciocardiodental Syndrome), Syndromic, Microphthalmia 3 (Microphthalmia and Esophageal Atresia Syndrome), Syndromic Microphthalmia 5, Syndromic Microphthalmia 6, Syndromic Microphthalmia 7, (Midas Syndrome), Syndromic Microphthalmia 9 (Matthew-Wood Syndrome), Syndromic Microphthalmia 11, Syndromic Microphthalmia 12, Syndromic Microphthalmia 13, Syndromic Microphthalmia 14, Tarp Syndrome, Tay-Sachs Disease (GM2-Gangliosidosis, Type I), Thiel-Behnke Corneal Dystrophy, Turner Syndrome, Tyrosinemia, Type II, Vacterl Association with Hydrocephalus, Von Hippel-Lindau Syndrome, Wagner Syndrome, Watson Syndrome, Wieacker-Wolff Syndrome, Wilson Disease, Achromatopsia, Alagille Syndrome, Aniridia, Anterior Segment Mesenchymal Dysgenesis, Axenfeld-Rieger Syndrome, Charge Syndrome, Cockayne Syndrome, Glaucoma, Congenital, Glaucoma, Open Angle Juvenile Onset, Jackson-Weiss Syndrome, Pfeiffer Syndrome, Prader-Willi Syndrome, Ref Sum Disease, Rubinstein-Taybi Syndrome, Normal-Tension Glaucoma, Oguchi Disease, Saethre-Chotzen Syndrome, Simpson-Golabi-Behmel Syndrome, Tuberous Sclerosis, Vitelliform Macular Dystrophy, Adult-Onset, Wolfram Syndrome, Alport Syndrome, Angelman Syndrome, Bardet Biedl Syndrome, Basal Cell Nevus Syndrome, Beckwith-Wiedemann Syndrome, Blue-Cone Monochromacy, Branchiootorenal Syndrome, Charcot-Marie-Tooth Disease, Cone-Rod Dystrophy, Congenital Disorder of Glycosylation, Congential Fibrosis of Extraocular Muscles, Congenital Nystagmus, Congenital Stationary Night Blindness, Cornelia de Lange Syndrome, Dyskeratosis Congenita, Ehlers-Danlos Syndrome, Fuch's Endothelial Corneal Dystrophy, Glaucoma, Open Angle Adult Onset, Hermansy-Pudlak Syndrome, Joubert Syndrome, Kearns-Sayre Syndrome, Leber Congenital Amaurosis, Leber Hereditary Optic Neuropathy, Leigh Syndrome, Peters' Anomaly Retinitis Pigmentosa, Muscular Dystrophy-Dystroglycanopathy, Myotonic Dystrophy, Niemann-Pick Disease, Noonan Syndrome, Neuronal Ceroid Lipofuscinosis, Oculocutaneous Albinism, Optic Atrophy, Oral-Facial-Digital Syndrome, Osteogenesis Imperfecta, Senior-Loken Syndrome, Septic-Optic Dysplasia (de Morsier Syndrome), Spastic Paraplegia, Stickler Syndrome, Treacher Collins Syndrome, Usher Syndrome, Waardenburg Syndrome, Weill-Marchesani Syndrome, and Xeroderma Pigmentosum.

In some embodiments, multiple injections may be performed over time to allow continuation of therapy. The injection of therapeutic may be accompanied by another agent that enables multiple deliveries. For e.g. AAV delivery is limited by immune response to AAV which usually limits the AAV usage to a single time treatment, a limitation commonly associated with intravitreal injection, and while sub-retinal injection is immune privileged, the damaged and diseased retina does not tolerate multiple injections without trauma. Another agent (such as ImmTOR) that suppresses this response can be injected prior, in combination, or after the AAV injection to mitigate the immune response and enable AAV therapy at multiple time points. This allows one to titrate the dose to patient response as necessary.

In some embodiments, the route of administration is by injection into the SCS. In some embodiments, the genetic disease or disorder is diagnosed by gene sequencing such as including, but not limited to, Sanger sequencing, next generation sequencing, high-throughput screening, exome sequencing, Maxam-Gilbert sequencing, chain-termination methods, shotgun sequencing, Bridge polymerase chain reaction, single molecule real-time sequencing, ion torrent sequencing, pyrosequencing, sequencing by synthesis, combinatorial probe anchor synthesis, sequencing by ligation and nanopore sequencing. In some embodiments, the ocular disease or disorder is diagnosed by an eye exam, an ophthalmoscope, ocular coherence tomography, retinal scanning, fluorescein staining, conjunctival staining, color vision testing, optic disc imaging, nerve fiber layer analysis, corneal topography, electro-diagnostic testing, fluorescein angiography, photography of the eye, specular microscopy, visual field testing, ultrasound of the eye and combinations thereof.

In some embodiments, a patient presents with elevated intraocular pressure and is diagnosed with early stage juvenile primary open angle glaucoma before significant optic nerve damage has occurred after being examined with an ophthalmoscope. A blood sample is drawn and sent for genetic testing, which determines that the patient has a mutation in the olfactomedin domain of his myocilin (MYOC) gene, mutation Y437H, that is likely implicated in causing the disease, leading to a diagnosis of myocilin-associated primary open angle glaucoma.

The patient is then treated by dosing with the injection system, administering microRNA complementary to the first 22 bases of mRNA for the MYOC gene formulated in aqueous solution of a self-assembling hydrogel with beta-cyclodextrin and EDTA as permeation enhancers. Prior to use, the injection is stored as a lyophilized powder in separate vials from the diluent. Following injection, the hydrogel self-assembles in the SCS after delivery providing sustained delivery of the microRNA that suppresses myocilin expression, leading to a reduced accumulation of myocilin in the trabecular meshwork, resulting in reduced intraocular pressure, thereby reducing the probability of sustaining optic nerve damage for the patient.

In another specific embodiment, a male child presents with night blindness and on exam is found to have reduced visual field and some retinal degeneration. A blood sample is drawn and sent for genetic testing, which determines that the patient has a mutation in his CHM gene, containing part or the entirety of the CHM gene sequence as described, for example, in https://www.uniprot.org/uniprot/P24386, incorporated herein by reference in its entirety, which encodes RAB escort protein 1 (REP1), which supports a diagnosis of early stage choroideremia.

The patient is then treated by dosing with the injection system, in which lyophilized AAV2 vector containing a retinal specific promoter, derived from the rhodopsin kinase (RK) promoter gene expressed in rods and cones, connected to the human CHM gene, has been reconstituted with its aqueous diluent prior to injection. On reconstitution, the injection agent solution contains approximately 1013 AAV vectors per milliliter. Once injected, the RK promoter and human CHM gene will be stably transfected into photoreceptor cells, where the corrected form of REP 1 will be expressed, treating the patient's choroideremia.

In another specific embodiment, an elderly patient presents with central vision defects. On routine retinal examination, drusen are detected. Fluorescein angiography demonstrates leaky choroidal vasculature, confirmed by the presence of sub-retinal fluid accumulation observed on optical coherence tomography (OCT). The patient is diagnosed with early stage neovascular age-related macular degeneration (AMD).

The patient is then treated by dosing with the injection system, in which 21-24 nucleotide short interfering RNA (siRNA) sequences complementary to portions the mRNA of one or more of the following alone or in combination of, vascular endothelial growth factor (VEGF), any of its subtypes including, but not limited to VEGF-A, VEGF-A121, VEGF-A165, VEGF-A189, VEGF-A206 VEGF-B, VEGF-C, VEGF-D, VEGF receptors (VEGFRs), VEGFR-1, VEGFR-2, VEGFR-3, NOTCH regulated ankyrin repeat protein (NRARP), and other angiogenesis promoting proteins encoding genes. The siRNA is delivered in a suspension of liposomal carriers. Following delivery, the siRNA knocks down expression of the angiogenesis promoting protein or proteins thereby preventing additional choroidal capillary growth and causing capillary regression yielding reduced choroidal capillary retinal and macular invasion and improved central vision. In a specific embodiment, the siRNA is targeted to knock down VEGFR-2, which has a gene sequence or isoforms thereof as described in https://www.uniprot.org/uniport/P35968, incorporated herein in its entirety.

In another specific embodiment, a patient diagnosed with neovascular AMD or diabetic retinopathy is treated by dosing with the injection system, in which an AAV vector, or other transfection vector, contains a gene that when transcribed produces an RNA sequence that is complementary to at least a portion of the mRNA that is translated into VEGFR-2. In delivering this gene therapy to the SCS, the choroidal capillaries, also referred to as choriocapillaris, contact the delivered therapeutic targeted at transfecting those cells expressing VEGFR-2. On transfection, the siRNA or shRNA vectors that are transcribed knock down or knock out VEGFR-2 production thereby reducing neovascularization to treat AMD or diabetic retinopathy.

In some embodiments, the physician may be presented with a suprachoroidal injection assembly or kit, which includes (1) a volume of the injection agent comprising one or more therapeutic agent formulations, i.e. active agent formulations, for example, containing an effective amount of an agent useful for treating a condition of an eye of a patient; (2) an injection system as described above and (3) optionally, an injector to facilitate ejection of the injection agent into and through the injection system membrane.

As described earlier, the agent formulation can comprise of various forms, such as solutions and suspensions of various viscosity. The entire kit is sterile including the formulation, injection system, and facilitating injector.

In some embodiments, the total volume of the active agent formulation to be injected in the suprachoroidal space is preferably in the range of approximately 0.01-0.5 mL. In some embodiments, the active agent may be provided in a lyophilized form and an accompanying diluent to create the suspension at the time of injection. In some embodiments, the active agent may be premixed. In some embodiments, the injection system may be prefilled with premixed formulation. In some embodiments, the user may fill the injection system immediately prior to administering the therapeutic formulation to the patient. In some embodiments, the injection system may contain multiple chambers with frangible separation. In some embodiments, the puncture element has initial penetrating length of 0.01 to 3 mm and the puncture element extends further while performing injection. In some embodiments, the injection system and injection facilitator can be preassembled with prefilled formulation and ready for use without any further assembly. In some embodiments, entire kit is packaged in a single pouch/tray to maintain sterility. In some embodiments, where components are packaged separately or in a combination. In some embodiments, the kit is sterilized together or separately by one of the sterilization methods including but not limited to autoclave, ethylene oxide, gamma radiation etc.

In some embodiments, where the components are present in a secondary package. In some embodiments, the kit is stored as a set at low enough temperature to extend the life of the active pharmaceutical agent. In some embodiments, the formulation is stored at low temperature separately while the rest of kit is stored at room temperature.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:
1. An injection system comprising:
a syringe barrel defining a lumen between a proximal end and a distal end;
a first sealing element moveably disposed within the lumen;
a second sealing element moveably disposed within the lumen proximal to the first sealing element, wherein the first sealing element and the second sealing element form a seal with the lumen and define an injection chamber between them;
a puncture element extending from a distal end of the first sealing element, the puncture element being in fluid communication with the injection chamber to deliver an injection agent from the injection chamber into a space in a tissue of a patient; and
a unidirectional stop disposed in the syringe barrel between the first sealing element and the second sealing element, the unidirectional stop being configured to;

contact the first sealing element during pre-insertion of the puncture element into the tissue, prevent a proximal movement of the first sealing element past the unidirectional stop during delivery of the injection agent, and allow the second sealing element to pass through the unidirectional stop to contact the first sealing element after delivery of the injection agent.

2. The system of claim 1, wherein the unidirectional stop comprises a section of the syringe barrel having a reduced diameter wherein the first sealing element has a diameter sufficiently larger than the reduced diameter such that the first sealing element cannot pass through the section while the second sealing element is configured to pass through the section to contact the first sealing element.

3. The system of claim 1, wherein the unidirectional stop comprises a portion of an inner surface of the syringe barrel having a friction coefficient sufficient to prevent the proximal movement of the first sealing element.

4. The system of claim 1, wherein the unidirectional stop comprises a mechanical stop.

5. The system of claim 1, wherein the unidirectional stop comprises a foldable stop is disposed between the first sealing element and the second sealing element, the foldable stop being configured to prevent a proximal movement of the first sealing element past the foldable stop and being configured to fold upon application of a force in the distal direction on the foldable stop to allow the second sealing element to pass through the foldable stop to contact the first sealing element.

6. The system of claim 1, wherein the first sealing element is shaped such that a first frictional or sliding force on the first sealing element in a proximal direction is higher than a second frictional or sliding force on the first sealing element in the distal direction and is higher than a force of insertion of the puncture element into the tissue.

7. The system of claim 1, wherein, in a relaxed state, the first sealing element has a size that is between 1.01 to 2 times larger than a size of the lumen of the syringe barrel.

8. The system of claim 1, wherein, in a relaxed state, the first sealing element has a size that is between 1.01 to 1.10 times larger than a size of the lumen of the syringe barrel.

9. The system of claim 1, wherein an inner surface of the syringe barrel is modified to increase friction between the inner surface of the syringe barrel and the first sealing element.

10. The system of claim 1, further comprising a lock disposed distally of the first sealing element and configured to selectively lock the first sealing element in place.

11. The system of claim 10, wherein the lock comprises a sealed compartment defined in the lumen of the syringe barrel distal to the first sealing element, an incompressible substance inside the compartment, and a valve to release the incompressible substance from the compartment, such that when the valve is closed, a distal movement of the first sealing element is prevented and, when the valve is open, the distal movement of the first sealing element is allowed.

12. The system of claim 1, further comprising a touch trigger mechanism between the first sealing element and the second sealing element, the touch trigger mechanism is configured to deploy when the first sealing element comes in contact with the second sealing element to prevent a distal movement of the first sealing element.

13. The system of claim 1, further comprising a fill port disposed on a surface of the syringe barrel and being in fluid communication with the injection chamber.

14. The system of claim 13, wherein the fill port comprises:

a receptacle disposed on an outside surface of the syringe barrel and configured to receive a vial;

a flowpath connecting the receptacle and the injection chamber;

a self-sealing member configured to seal the flowpath; and a puncture element disposed in the receptacle, the puncture element being configured to pierce through the self-sealing member to fluidly connect a vial comprising the injection agent and received in the receptacle with the injection chamber.

15. The system of claim 14, wherein the puncture element is moveable relative to the receptacle such that, when the vial is received in the receptacle, the puncture element is moved toward the injection chamber to pierce the self-sealing member and to fluidly connect the vial with the injection chamber, and when the vial is removed from the receptacle, the puncture element is moved away from the injection chamber, thereby allowing the self-sealing member to seal the flowpath.

16. The system of claim 1, wherein a support element is disposed about a distal portion of the puncture element, the support element being moveable in relation to the puncture element and the syringe barrel.

17. The system of claim 1, wherein the injection chamber comprises a first chamber and a second chamber, wherein a chamber sealing portion of the second sealing element fluidly isolates the first chamber from the second chamber, such that a movement of the chamber sealing portion fluidly connects the first and second chambers.

18. The system of claim 1, wherein the injection chamber comprises a first chamber and a second chamber, wherein the first chamber and the second chamber are fluidly isolated from one another when the second sealing element is in an initial position and wherein a movement of the second sealing element fluidly connects the first and second chambers.

19. The system of claim 1, wherein the second sealing element is configured to engage the first sealing element and to withdraw the first sealing element and the puncture element into the syringe barrel.

20. A kit for injection of an injection agent into a tissue comprising:

an injection system comprising:

a syringe barrel defining a lumen between a proximal end and a distal end;

a first sealing element moveably disposed within the lumen;

a second sealing element moveably disposed within the lumen proximal to the first sealing element, wherein the first sealing element and the second sealing element form a seal with the lumen and define an injection chamber between them;

a puncture element extending from a distal end of the first sealing element, the puncture element being in fluid communication with the injection chamber to deliver an injection agent from the injection chamber into a space in a tissue of a patient;

a unidirectional stop disposed in the syringe barrel between the first sealing element and the second sealing element, the unidirectional stop being configured to:

contact the first sealing element during pre-insertion of the puncture element into the tissue,

prevent a proximal movement of the first sealing element past the unidirectional stop during delivery of the injection agent, and allow the second sealing element to pass through the unidirectional stop to contact the first sealing element after delivery of the injection agent; and a volume of the injection fluid comprising one or more injection agent formulations.

21. The kit of claim 20, wherein the injection system further comprises a lock disposed distally of the first sealing element and configured to selectively lock the first sealing element in place.

22. The kit of claim 20, wherein the injection system further comprises a touch trigger mechanism between the first sealing element and the second sealing element, the touch trigger mechanism is configured to deploy when the first sealing element comes in contact with the second sealing element to prevent a distal movement of the first sealing element.

23. The kit of claim 20, wherein the injection system further comprises a fill port disposed on a surface of the syringe barrel and being in fluid communication with the injection chamber.

24. The kit of claim 23, wherein the fill port comprises:

a receptacle disposed on an outside surface of the syringe barrel and configured to receive a vial;

a flowpath connecting the receptacle and the injection chamber;

a self-sealing member configured to seal the flowpath; and the puncture element disposed in the receptacle, the puncture element being configured to pierce through the self-sealing member to fluidly connect a vial received in the receptacle with the injection chamber.

25. The kit of claim 20, wherein the injection chamber comprises a first chamber and a second chamber, wherein a chamber sealing portion of the second sealing element fluidly isolates the first chamber from the second chamber, such that a movement of the chamber sealing portion fluidly connects the first and second chambers.

26. The kit of claim 20, wherein the injection chamber comprises a first chamber and a second chamber, wherein the first chamber and the second chamber are fluidly isolated from one another when the second sealing element is in an initial position and wherein a movement of the second sealing element fluidly connects the first and second chambers.

* * * * *